US012588811B2

(12) United States Patent
Serafini et al.

(10) Patent No.: US 12,588,811 B2
(45) Date of Patent: Mar. 31, 2026

(54) MODULAR PLATFORM FOR OCULAR EVALUATIONS

(71) Applicant: Icahn School of Medicine at Mount Sinai, New York, NY (US)

(72) Inventors: Randal Alexander Serafini, New York, NY (US); Andrew Jinrui Warburton, New York, NY (US); Claudio Randal Serafini, Sunnyvale, CA (US); Aashay Dineshkumar Patel, New York, NY (US); Margarita Labkovich, New York, NY (US); Aly Al-Amyn Valliani, New York, NY (US); Sumeet Murarka, Latham, NY (US); Avner Sadot, Tel Aviv (IL); Ilana Teicher, Tel Aviv (IL); Ori Jacobi, Tel Aviv (IL); Tal Preger Galili, Tel Aviv (IL)

(73) Assignee: Icahn School of Medicine at Mount Sinai, New York, NY (US)

( * ) Notice: Subject to any disclaimer, the term of this patent is extended or adjusted under 35 U.S.C. 154(b) by 428 days.

(21) Appl. No.: 17/919,003

(22) PCT Filed: Apr. 15, 2021

(86) PCT No.: PCT/US2021/027544
§ 371 (c)(1),
(2) Date: Oct. 14, 2022

(87) PCT Pub. No.: WO2021/211886
PCT Pub. Date: Oct. 21, 2021

(65) Prior Publication Data
US 2023/0233076 A1      Jul. 27, 2023

Related U.S. Application Data

(60) Provisional application No. 63/155,213, filed on Mar. 1, 2021, provisional application No. 63/150,481, filed
(Continued)

(51) Int. Cl.
*G02B 3/00* (2006.01)
*A61B 3/024* (2006.01)
(Continued)

(52) U.S. Cl.
CPC ............ *A61B 3/113* (2013.01); *A61B 5/1128* (2013.01)

(58) Field of Classification Search
CPC .......... G02B 3/00; G02B 27/00; G02B 27/01; G02B 27/0093; G02B 27/017;
(Continued)

(56) References Cited

U.S. PATENT DOCUMENTS 8,902,315 B2    12/2014  Fisher et al.
2009/0105393 A1    4/2009  Jansen et al.
(Continued)

FOREIGN PATENT DOCUMENTS

CN        107224261        10/2017
CN        108 429 906        8/2018
(Continued)

OTHER PUBLICATIONS

"Extended European Search Report in EP Application No. 21789046. 6", Apr. 24, 2024, 11 pages.
(Continued)

*Primary Examiner* — Dawayne Pinkney
(74) *Attorney, Agent, or Firm* — IP Spring

(57) ABSTRACT

A screening platform enables comprehensive ocular evaluations. The screening platform includes a harness that is
(Continued)

600 configured to fit a head of a patient and that includes one or more electronic components that are operable to power an interchangeable module, a central processing unit (CPU) with a graphical processing unit (GPU), and the interchangeable module with communication capabilities to external computational devices, multiple display output devices, and several types of input devices from both an operator and a patient at-hand, wherein the interchangeable module is separable from the screening platform.

27 Claims, 15 Drawing Sheets

Related U.S. Application Data on Feb. 17, 2021, provisional application No. 63/010, 662, filed on Apr. 15, 2020.

(51) Int. Cl.
| | |
|---|---|
| *A61B 3/10* | (2006.01) |
| *A61B 3/113* | (2006.01) |
| *A61B 5/11* | (2006.01) |
| *A63F 13/53* | (2014.01) |
| *G02B 27/01* | (2006.01) |

(58) Field of Classification Search
CPC ..................... G02B 2027/014; G02B 27/0103; G02C 7/00; G02C 7/024; A61F 13/53; A61F 9/026; A61B 3/02; A61B 3/102; A61B 3/113; A61B 3/1015; A61B 3/1225; A61B 3/005
USPC ............ 359/618, 629, 630, 13–14; 345/7–9; 351/200, 205, 209, 210, 221, 222, 245, 351/246, 41, 159.01, 159.75; 348/115
See application file for complete search history.

(56) References Cited

U.S. PATENT DOCUMENTS

| | | | |
|---|---|---|---|
| 2009/0153796 A1 | 6/2009 | Rabner | |
| 2017/0031435 A1 | 2/2017 | Raffle et al. | |
| 2017/0153672 A1 | 6/2017 | Son et al. | |
| 2017/0172406 A1 | 6/2017 | Pamplona et al. | |
| 2017/0273552 A1* | 9/2017 | Leung ................... | A61B 3/005 |
| 2017/0337737 A1 | 11/2017 | Edwards et al. | |
| 2018/0008141 A1 | 1/2018 | Krueger | |
| 2018/0217382 A1 | 8/2018 | Urbach et al. | |
| 2018/0308288 A1* | 10/2018 | Harscoet ............. | G06F 3/04815 |
| 2019/0104650 A1* | 4/2019 | Mcginty ............ | H05K 7/20963 |
| 2019/0240569 A1* | 8/2019 | Kuwatani ............... | G06F 3/012 |
| 2019/0380875 A1 | 12/2019 | Esmonde | |
| 2020/0050257 A1* | 2/2020 | Lee .......................... | A61B 3/14 |
| 2020/0093361 A1 | 3/2020 | Beecher et al. | |
| 2022/0000556 A1* | 1/2022 | Casey .................... | G16H 50/50 |

FOREIGN PATENT DOCUMENTS

| | | |
|---|---|---|
| CN | 209471305 | 10/2019 |
| CN | 110742575 | 2/2020 |
| WO | WO 2019/109058 | 6/2019 |
| WO | WO 2021/022028 | 2/2021 |

OTHER PUBLICATIONS

"International Report on Patentability in International Application No. PCT/US2021/027544", Oct. 27, 2022, 10 pages.
"International Search Report and Written Opinion in International Application No. PCT/US21/027544", Aug. 3, 2021, 12 Pages.
"CN First Office Action in Chinese Application No. 202180042851. 0", Jan. 8, 2026.

* cited by examiner

300

400

900

29

1000

1100

1200

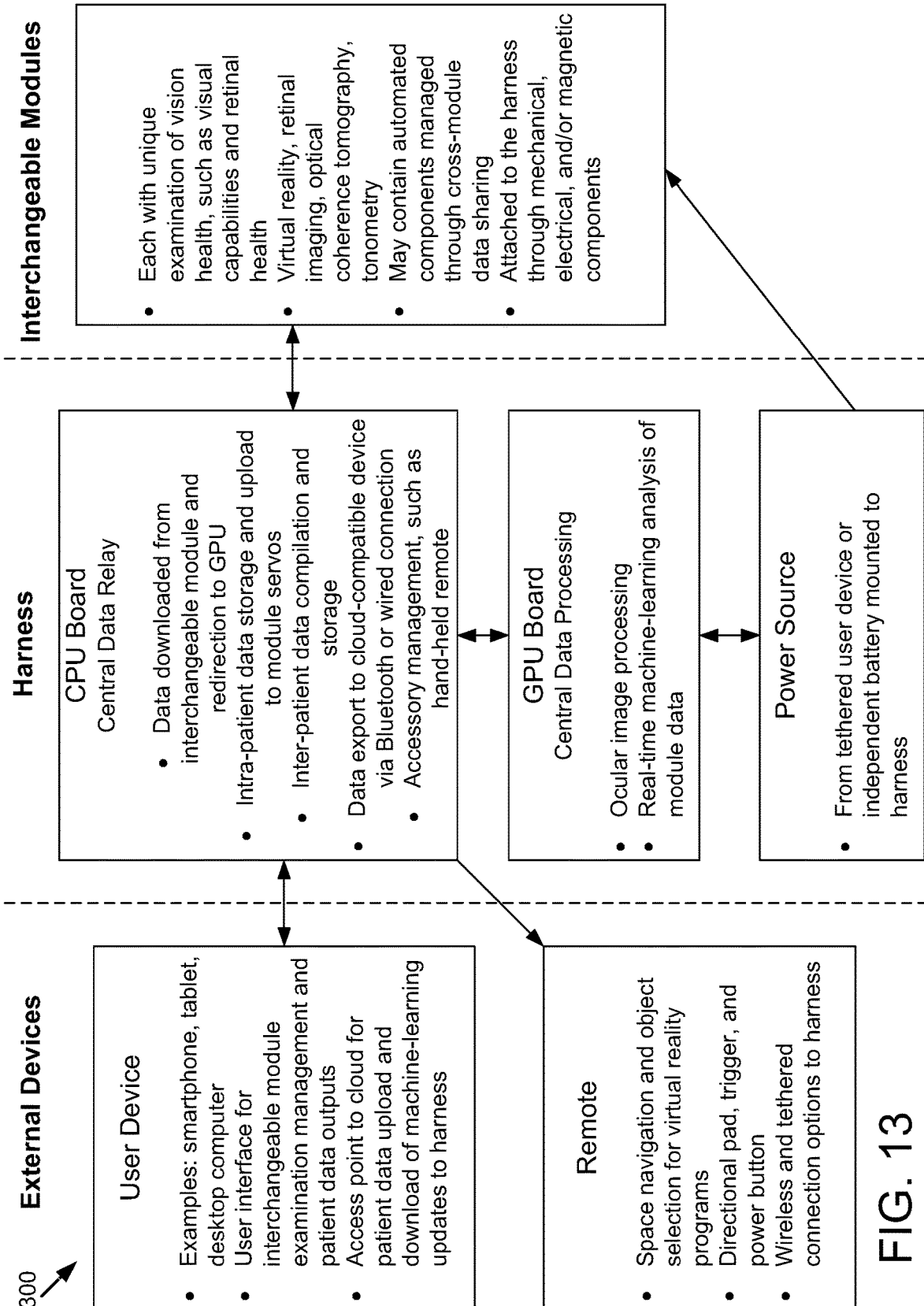

Interchangeable Modules

- Each with unique examination of vision health, such as visual capabilities and retinal health
- Virtual reality, retinal imaging, optical coherence tomography, tonometry
- May contain automated components managed through cross-module data sharing
- Attached to the harness through mechanical, electrical, and/or magnetic components

Harness

CPU Board
Central Data Relay

- Data downloaded from interchangeable module and redirection to GPU
- Intra-patient data storage and upload to module servos
- Inter-patient data compilation and storage
- Data export to cloud-compatible device via Bluetooth or wired connection
- Accessory management, such as hand-held remote

GPU Board
Central Data Processing

- Ocular image processing
- Real-time machine-learning analysis of module data

Power Source

- From tethered user device or independent battery mounted to harness

External Devices

1300

User Device

- Examples: smartphone, tablet, desktop computer
- User interface for interchangeable module examination management and patient data outputs
- Access point to cloud for patient data upload and download of machine-learning updates to harness

Remote

- Space navigation and object selection for virtual reality programs
- Directional pad, trigger, and power button
- Wireless and tethered connection options to harness

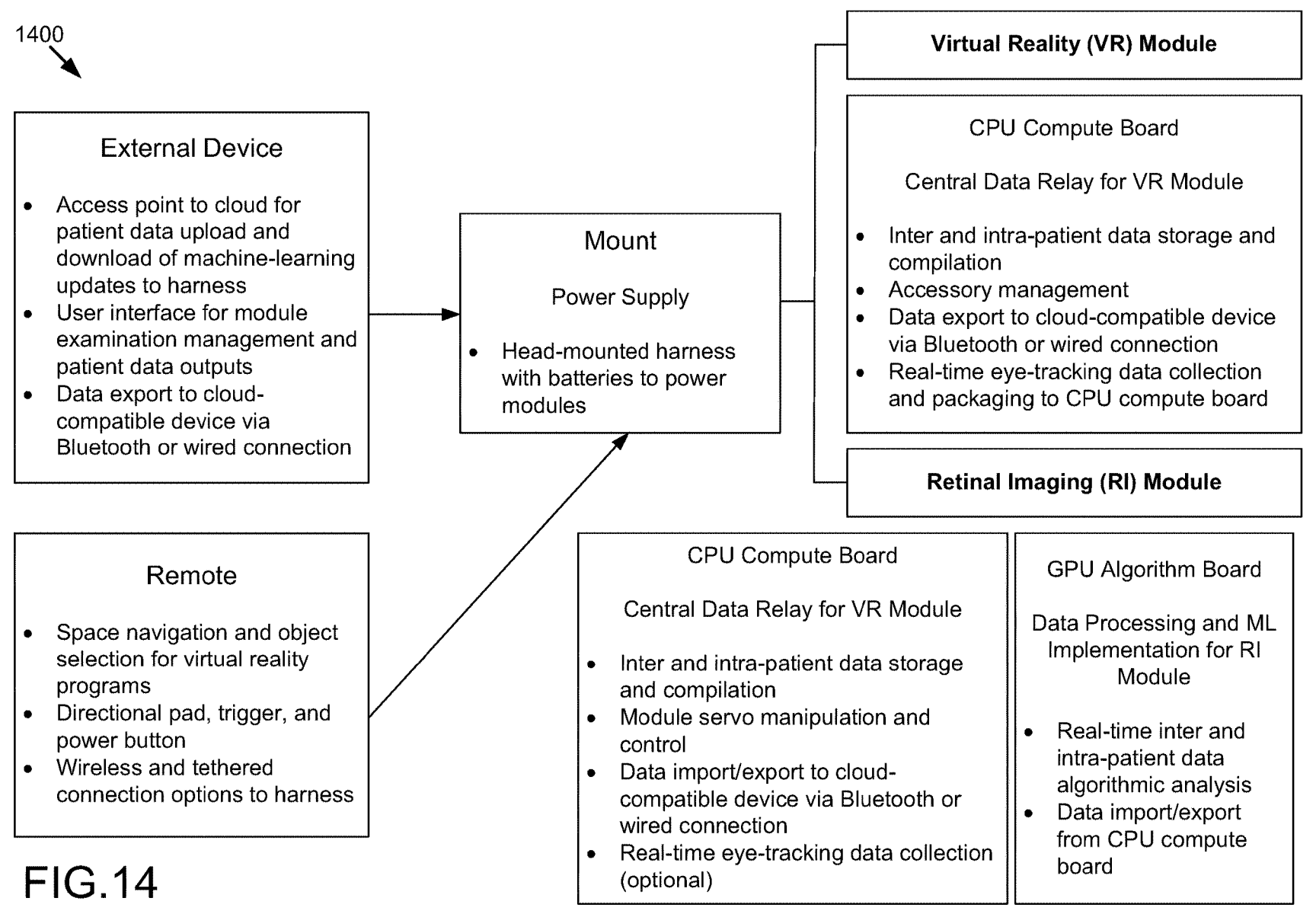

Virtual Reality (VR) Module

CPU Compute Board

Central Data Relay for VR Module

- Inter and intra-patient data storage and compilation
- Accessory management
- Data export to cloud-compatible device via Bluetooth or wired connection
- Real-time eye-tracking data collection and packaging to CPU compute board

Retinal Imaging (RI) Module

GPU Algorithm Board

Data Processing and ML Implementation for RI Module

- Real-time inter and intra-patient data algorithmic analysis
- Data import/export from CPU compute board CPU Compute Board Central Data Relay for VR Module

- Inter and intra-patient data storage and compilation
- Module servo manipulation and control
- Data import/export to cloud-compatible device via Bluetooth or wired connection
- Real-time eye-tracking data collection (optional)

Mount

Power Supply

- Head-mounted harness with batteries to power modules

External Device

- Access point to cloud for patient data upload and download of machine-learning updates to harness
- User interface for module examination management and patient data outputs
- Data export to cloud-compatible device via Bluetooth or wired connection Remote

- Space navigation and object selection for virtual reality programs
- Directional pad, trigger, and power button
- Wireless and tethered connection options to harness

FIG.14

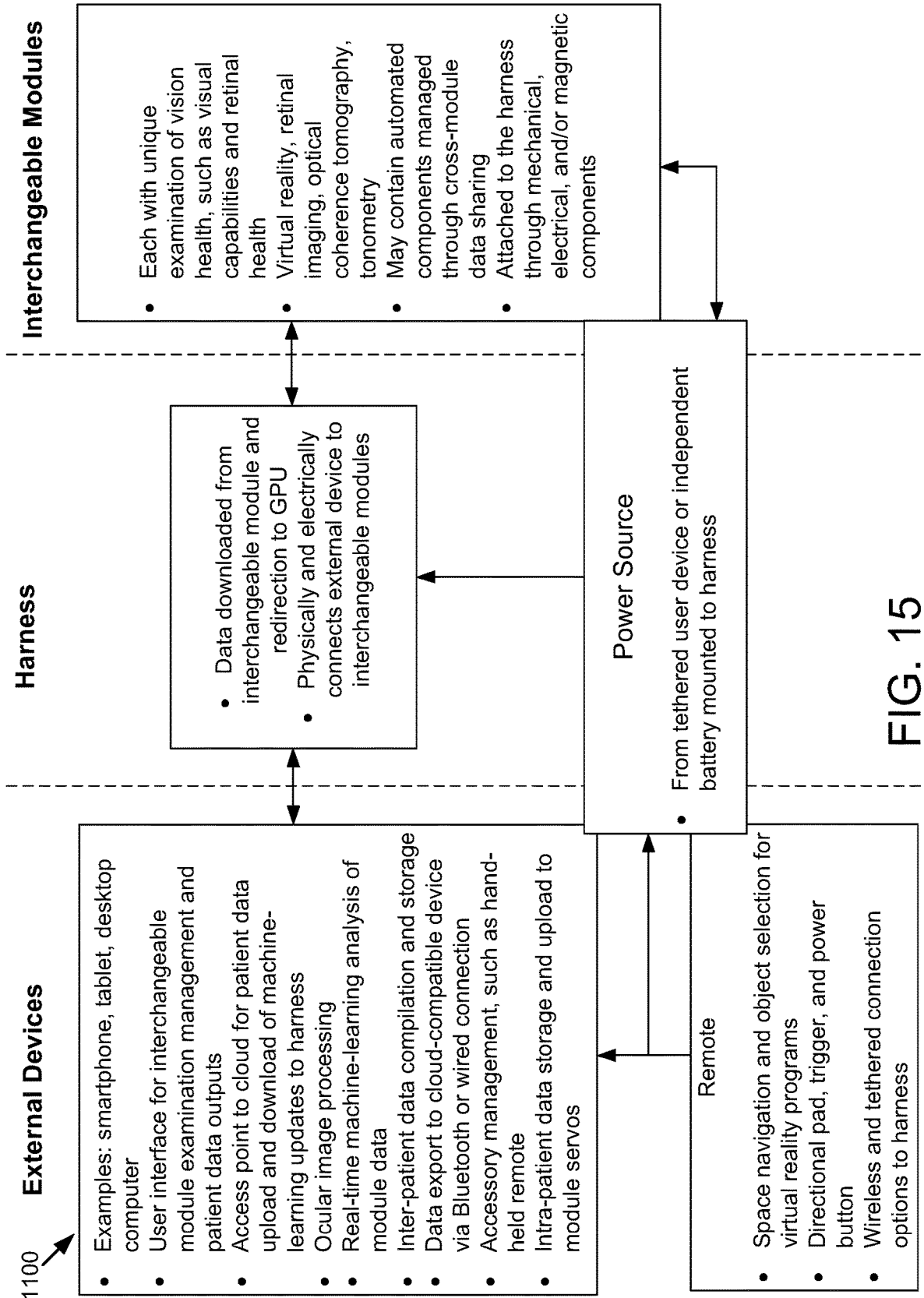

Interchangeable Modules

- Each with unique examination of vision health, such as visual capabilities and retinal health
- Virtual reality, retinal imaging, optical coherence tomography, tonometry
- May contain automated components managed through cross-module data sharing
- Attached to the harness through mechanical, electrical, and/or magnetic components

Harness

- Data downloaded from interchangeable module and redirection to GPU
- Physically and electrically connects external device to interchangeable modules

Power Source

- From tethered user device or independent battery mounted to harness

External Devices

1100

- Examples: smartphone, tablet, desktop computer
- User interface for interchangeable module examination management and patient data outputs
- Access point to cloud for patient data upload and download of machine-learning updates to harness
- Ocular image processing
- Real-time machine-learning analysis of module data
- Inter-patient data compilation and storage
- Data export to cloud-compatible device via Bluetooth or wired connection
- Accessory management, such as hand-held remote
- Intra-patient data storage and upload to module servos

Remote

- Space navigation and object selection for virtual reality programs
- Directional pad, trigger, and power button
- Wireless and tethered connection options to harness

FIG. 15

MODULAR PLATFORM FOR OCULAR EVALUATIONS

CROSS-REFERENCE TO RELATED APPLICATION

This application is a § 371 national stage of PCT International Application No. PCT/US21/27544, entitled "Modular Platform For Ocular Evaluations" filed on Apr. 15, 2021, which claims the benefit of priority under 35 U.S.C. §111(a) as a continuation of U.S. Provisional Patent Application Ser. No. 63/010,662, entitled "Modular Platform for Virtual Reality Visual Screening, Eye Imaging, and Clinical Diagnosis," filed on Apr. 15, 2020; U.S. Provisional Patent Application Ser. No. 63/150,481, entitled "Head-Mounted Modular Device for Health Examinations," filed on Feb. 17, 2021; U.S. Provisional Patent Application Ser. No. 63/155, 213, entitled "Head-Mounted Modular Device for Health Examinations," filed on Mar. 1, 2021, which are hereby incorporated by reference in their entirety for all purposes.

BACKGROUND

There exists a significant deficit in the accessibility, affordability, and reliability of vision screening apparatuses within the United States. Although over 240,000 Americans are diagnosed with blindness or severe vision loss annually, 61% of counties in the U.S. have either a low ophthalmologist (<2.95/100,000 residents) or a low optometrist (<11/100,000 residents) ratio, which severely reduces vision screening capabilities. Globally the situation is significantly worse. Out of a world population of about 7.7 billion people, at least 2.2 billion people have a vision impairment or blindness, of whom at least 1 billion have a vision impairment that could have been prevented or has yet to be addressed.

The most common ophthalmic pathologies in the United States are refractive errors, age-related macular degeneration, cataract, diabetic retinopathy, glaucoma, amblyopia, and strabismus. Internationally, the most common ophthalmic pathologies are cataract (51%), undetermined (21%), glaucoma (8%), and age-related macular degeneration (5%). Each pathology requires a unique set of techniques and tools outlined below to properly make a diagnosis. Examples of the need for unique tools to assess certain pathologies include the following: eye chart testing for visual acuity impairments, retinal photography and perimetry for diabetic retinopathy, tonometry (intraocular pressure measurements) and ocular coherence tomography (OCT) for glaucoma, slit lamp microscopy for primary angle closures, and distortion grids and OCT for age-related macular degeneration.

As the examples above illustrate, there are many diseases and disorders of the eye that require specialist equipment to diagnose during routine eye testing. It is important to be able to detect these diseases and disorders promptly because many of them, if left untreated, will lead to progressive and irreversible loss of eyesight. Expanded ocular abnormality screenings may also identify underlying non-ophthalmic pathological conditions of the patient that can be more effectively managed with earlier treatment, including diabetes, high blood pressure, psychological conditions, ocular or cerebral injury, pharmacologic screening, and neurologic tumors. The eye is the only place in the body where a doctor can have an unobstructed view of blood vessels, nerves and connecting tissue, without invasive intervention. The wide range of ophthalmic equipment needed to perform these tests is financially daunting for all, but the best equipped ophthalmologist's offices provide both the training and means for optometrists who perform basic eye tests and primary care physicians who see much larger patient populations. Several companies and research groups are exploring the possibility of using virtual reality headsets (VR headsets) to perform visual acuity testing and optical pathology screenings. For example, the present assignee, Retina Technologies Inc., a Delaware company based in New York City, NY, has developed a headset that can perform visual function tests, such as visual acuity, contrast sensitivity, distortion grid, color blindness, and perimetry, at much lower costs than conventional equipment. In addition to low cost, another advantage of the VR headsets is their simplicity of use, allowing non-ophthalmic medical professionals, such as optometrists, primary care physicians, and retail personnel (opticians and pharmacists) to perform these complex tests and provide an effective screening to identify those patients who have an ophthalmic pathology that needs specialist care.

Recent clinical trials have established the accuracy and minimal training requirements of VR headsets, particularly in vision examinations such as perimetry. This has enabled for more portable and widespread screening of prevalent, chronic diseases such as glaucoma. Furthermore, the ability to provide head-mounted tests, such as perimetry, offers the advantage of testing in comfortable seated positions or even patients who need to be reclined.

Many commercially available VR headsets have a field of view (FOV) that can range from 60 degrees to 210 degrees. Given the breadth of VR headset's FOV, a VR headset system can also be implemented in research for stereopsis, screening cognitive decline, and measuring ocular misalignment. Many commercially available VR systems also have integrated eye tracking, allowing for gaze recording for measurement of saccades or validation of proper perimetry testing, as well as for testing of oculomotor function.

As discussed above there are many different ophthalmic diagnostic tests that require a wide diversity of diagnostic test equipment. One of the major limitations of current VR headsets for ophthalmic applications is the limited range of ophthalmic tests that a VR headset alone can perform, because of space confinements and dependence on screens and eye tracking rather than other ophthalmic technologies such as retinal cameras to provide a more comprehensive overview of ocular health. Therefore, a VR headset alone is currently inadequate to deliver a comprehensive vision screening. Commercially available, portable devices exist that must be manually held against a patient's head and have single-use ophthalmic functions, such as retinal photography (RetinaVue 700 Imager), or placed on a table in front the patient, such as portable OCT (Notal Home OCT).

There does not currently exist an extensive head-mounted platform to perform comprehensive ophthalmologic testing for patients. A platform beneficial to the field of vision screening would embody an end-to-end solution capable of performing both functional and anatomical assessments without the need for independent, non-integratable devices.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

Conventional VR headsets available for ophthalmology testing are limited due to their ability to screen only functional and potentially oculomotor deficits through vision tests and eye tracking, respectively. There does not appear to currently exist a platform that can provide both a comprehensive functional and oculomotor vision screening and identify anatomical pathologies through assays such as retinal photography, tonometry, OCT, fluoroscopy, prismatic astigmatism testing, oculomotor exercises or keratometry. Incorporating modularity into a head-mounted ophthalmic apparatus enables for increased portability, speed, and affordability of vision screenings, assuming miniaturization of existing technologies is feasible. By this method, an operator or patient could essentially remove the virtual reality component of a headset and attach a different component (from here on referred to as an interchangeable module) for testing such as retinal photography. Because this technology would enable for a decentralization of quantitative vision testing to non-vision specialists, this system would benefit from standalone computational capabilities, including data analysis and referral recommendations to specialists. Furthermore, designing an "intelligent harness" to which the interchangeable modules can attach provides a centralized data processing, modular processing, and cloud integration platform enabling further access to patient data, increased control over the interchangeable modules by the technician, and increased real-time capabilities of the harness through the implementation of machine-learning algorithms to improve possible screening or diagnostics tests for patients without sacrificing time or performance.

While Khan and Susanibar in WO 2021/022028 describe a modular, head-mounted device, they place their focus on computational independence and sub-modularity of modules, essentially rendering the platform not immediately integratable, as one would be able to do with a computational anchor point, like the head harness proposed here. The need to modify a module through sub-modularity because of reliance in intra-module compute unnecessarily increases the complexity of a module and introduces substantial forward weight at the head. Furthermore, the application did not mention the use of advanced processing technologies for the purpose of head-mounted data analyses, creating a reliance on external devices for processing. The head mount in the Khan and Susanibar application consists of a) a basic mechanical attachment means (clips) that promote substantial movement at the head-mount when removing modules, reducing the immediate comparability of data between modules, and b) a method of anchoring a wire to an external power source to a module. No methods for counterbalancing the unnaturally high forward load a patient experiences from attaching relatively heavy ophthalmic technologies, such as a retinal camera, are mentioned. Furthermore, no effort was made to describe a method by which to transfer data between different modules or analyze data from several modules without the need for an external device. These shortcomings substantially limit the locations in which their technology can be successfully deployed. The system proposed here leverages an intelligent, computational anchor point for modules embodied by the head-mounted harness, allowing for a method of ophthalmic modularity that is not obvious in the prior art, and improves the utility of said system in a much broader audience. Additionally, the materials described in the description below are designed for medical applications of a head-mounted vision screening platform to allow for proper cleaning, sterility, and protection for the patient while not sacrificing strength of function of the components.

The proposed head-mounted screening platform is comprised of three main functional components: (1) a head-mounted harness; (2) on-board processing capabilities including several computer processing units (CPUs) and a graphics processing unit (GPU); and (3) interchangeable modules. For clarification, "on-board" will refer to anything on the harness or module, as opposed to an external device. The harness provides an attachment mechanism by which an interchangeable module can be placed directly in front of the user's eyes, and a strap or other means that further stabilizes the device on the patient's head. The CPU(s) may contain the microprocessor(s) and graphics processor(s) for operating the display, memory for running programs, data storage if needed, batteries or an external power jack for power and communications with external systems, for example, to upload new programs or download data. The GPU enables for on-harness data analytics, image analysis, and machine learning-mediated referral recommendations. The interchangeable module can contain components such as screens, lenses, a CPU, eye tracking cameras, and ophthalmic devices such as retinal cameras, keratometers, OCT units, and slit lamps, along with non-ophthalmic medical or therapeutic devices such as plastic screens, light filters, meshes, and bevels alone or in combination. The interchangeable modules also have communication capabilities with external computational devices, multiple display output devices, and several types of input devices from both an operator and a patient. The CPU and GPU components can be separate or combined chipsets (as seen in the A14 bionic processor with combined CPU and GPU or a Snapdragon XR2 CPU+ NVIDIA Tegra K1 GPU). The CPU and GPU processors are subject to change based on the current technology and those skilled in the craft may adapt them appropriately.

Each interchangeable module serves a unique functional purpose. For example, the interchangeable module may include a VR module that provides a display and associated optics, such as eye tracking cameras, for functional and oculomotor testing. The optical module is positioned in front of the eyes and connects to the mask-like aperture so that the wearer of the screening platform can see the display. An interchangeable module may also include other optical devices, such as retinal cameras with or without eye tracking equipment.

In contrast to prior art VR headsets with monolithic designs, the proposed screening platform utilizes a modular design, with an easily interchangeable module so that with different optical modules available, a wider range of functionality to perform additional ophthalmic tests can be incorporated into the headset that is not possible with a monolithic design. Furthermore, the system has a harness that serves as more than a physical mounting point on the head, providing power to modules, storing data acquired with each module, managing the interactions between modules if necessary, and analyzing the data for future output to on-board screens or external devices. This enables for standalone use in virtually any environment. The harness augments the headset computationally as well as the experience for both the patient and provider, as more real-time data can be processed while maintaining portability and comfort.

The most basic interchangeable module contains a display. The basic interchangeable module display includes a left and right screen at a resolution of at least 3840×2160 pixels (4K) to reduce aliasing and distortion of small displayed items. The screen is preferably made of LCD/LED/OLED/micromirror display technologies, but other display technologies that achieve at least similar performance may be used within the scope of the disclosed subject matter. The screen will typically be placed about 5 cm from each eyeball. Lenses are mounted between the screen and the eyes, so that the lenses can focus the light from the screen such that the wearer can perceive the image clearly. The interchangeable module is designed so that the patient may also don glasses during exams, which is essential for the detection of rapid, substantial vision loss due to conditions such as stroke.

By swapping the interchangeable optical modules, a wide range of ophthalmic diagnostics tests can be performed with a single screening platform. The optical unit is modular, so to perform a perimetry test for example, the interchangeable VR module includes a display, eye tracking, and software-embedded perimetry tests, such as a 10-2, 24-2, 30-2. Due to the nature of this VR module, an operator could also run other functional vision tests on the same VR module as well, such as color blindness, contrast sensitivity, visual acuity, and distortion grids. The display module can be adapted in multiple different configurations such as a single screen, binary screens (for each eye) or other configurations that one skilled in the craft would apply. The brightness of the VR module can easily be manipulated in the software, allowing for low luminance testing. Monocular testing can occur by "blacking out" one of the screens in software or by mechanical means such as a shutter over one of the screens.

If the next test needed was retinal photography, then the VR module would be removed and a retinal camera module would be attached to the harness. The development of an interchangeable module solves a major limitation with conventional VR headsets, allowing a patient to be tested comprehensively, quickly, easily and at lower cost than conventional methods, as multiple ophthalmic devices are needed for accurate diagnosis of a wide range of ophthalmic pathologies such as optic neuritis, diabetic retinopathy, glaucoma, etc. Acquisition of data from both function- and anatomy-assessing modules on a single, computational harness also allows for multidimensional data analysis on a single device, enabling for machine-learning analytics without the need for an external compute device, such as a laptop. Current in-office standards require data acquisition with several devices, rendering this type of centralized analysis much more challenging.

In some embodiments, a screening platform enables comprehensive ocular evaluations, wherein the screening platform is modular, comprising: a harness that is configured to fit the head of a patient and that includes one or more electronic components that are operable to power an interchangeable module, a first central processing unit (CPU) with a graphical processing unit (GPU) and associated computational hardware (random access memory (RAM), digital storage, wifi capabilities, etc.—collectively called "harness compute"), and the interchangeable module. The harness compute has communication capabilities to external computational devices, multiple display output devices on the interchangeable module or harness, and several types of input devices from both an operator and a patient at-hand, wherein the interchangeable module is separable from the screening platform.

In some embodiments, the harness includes a harness slide connector that couples one or more interchangeable modules to the harness and wherein the harness slide connector contains a second CPU. There are intentional advantages to this placement, including a rapid, two-way functional connection between the harness and the interchangeable module, as well as isolation of core harness processing units (CPU, GPU, RAM) in the event of a short circuit after interchangeable module attachment. This also provides the safest transition of interchangeable modules for the patients and an intuitive solution medical practitioners and technicians are familiar with.

In some embodiments, the first CPU stores data including pupillary coordinates acquired by the interchangeable module for use with one or more other interchangeable modules. This reduces the need for eye tracking integration into every module and uniquely streamlines the data between modules via the harness. In some embodiments, the first CPU or the GPU control, display, and process data from the one or more interchangeable modules by employing machine-learning algorithms. The machine-learning algorithms may include performing at least one of the following: optimization of the interchangeable modules and examination order, analysis of images to determine ocular pathology ranging from true physiologic deficit pathologies, contrast sensitivity, oculomotor function, visual acuity, color blindness, refractive errors, intraocular pressure, retinal imaging, tonometry, perimetry, eye-tracking, amblyopia assessment, keratometry, videographic slit lamp microscopy, microperimetry, optical coherence tomography, neurodegenerative disease screening, psychiatric conditions screening, fluoroscopy, oculomotor exercise coaching, pupillary diameter measurements, myopia vs hyperopia screening, corneal reflex measurements, saccade measurements, or astigmatism screening, wherein any of the optical examinations integrate within an electronic medical record.

In some embodiments, the one or more electrical components of the harness are selected from the group of rechargeable batteries, RAM, storage memory, data or power input and output ports, and an auxiliary port. In some embodiments, the interchangeable module is selected to perform at least one of the following optical examinations: visual function examinations, contrast sensitivity, oculomotor function, visual acuity, color blindness, refractive errors, intraocular pressure measurements, retinal photography, tonometry, perimetry, eye-tracking-mediated oculomotor testing, amblyopia assessment, keratometry, videographic slit lamp microscopy, microperimetry, optical coherence tomography, neurodegenerative and psychiatric disease screening, fluoroscopy, oculomotor exercise coaching, pupillary diameter measurements, saccade measurements, or astigmatism screening, wherein any of the optical examinations integrate within an electronic medical record. In some embodiments, the interchangeable module is configured for performing ocular screening for at least one of the following conditions: ophthalmic diseases, cognitive disorders, psychiatric disorders, neurodegenerative diseases, traumatic brain injury, pharmacologic side effects, or substance abuse. In some embodiments, the volume defined by an interchangeable module is less than or equal to a volume of 8000 cm$^3$ as to avoid overwhelming torque on the patient for up to a continuous 1 hour of use where a battery pack is mounted on the rear of the harness such that the battery pack counterweighs the mass of the interchangeable module on a head of the patient, otherwise creating damaging torque or discomfort that reduces testing accuracy without a counterbalance. In some embodiments, avoiding the overwhelming torque reduces dizziness from vestibular compensation of the patient.

In some embodiments, the power is redundantly provided by the harness—or interchangeable module-integrated or external device-connected batteries to enhance portability and remote use. These batteries can be recharged conventionally through alternating current (AC) power and direct connection via a power cable, redundantly charged while AC power is applied through the harness, or wirelessly charged through induction. In some embodiments, the first CPU includes means for wired or wireless communication to external systems, output displays, and processing operator and patient input. In some embodiments, analysis by a harness compute provides referral and further screening recommendations to a performing healthcare provider through a cross-analysis of functional and anatomical data from a same angle with respect to an eye of the patient due to direct modularity and immediate temporality. In some embodiments, results of ophthalmic tests are transferred automatically to an electronic health record associated with the patient through a wired or non-wired connection out from the harness. In some embodiments, the interchangeable module tracks pupillary eye tracking coordinates for eyes of the patient using at least one of the following illumination sources: visible light, infrared, near ultraviolet light, or narrow-band light. In some embodiments, the pupillary eye tracking coordinates from one module are used to guide coordinate-based tests and examinations for a separate interchangeable module, such as manual or automatic retinal camera alignment of a subsequent interchangeable module through one or more of lead screws, knobs, sliders, fine-tooth gears, or motors. In some embodiments, wireless or wired communication between the harness and an external device enables the operator to manage tests administered to the patient wearing the harness from the external device via data output from the harness.

In some embodiments, the harness further comprises a periorbital frame to which the interchangeable module is attached. In some embodiments, the periorbital frame includes a malleable material that causes the periorbital frame to be flush against a face of the patient to provide a dark environment for non-mydriatic examinations. In some embodiments, the screening platform further comprises an attachment platform that does not contact a face of the patient and a separable interchangeable module that contacts the face in a light-diminishing fashion. In some embodiments, the interchangeable module is lined with a malleable material to create a flush, light-proof seal against the face. In some embodiments, a third CPU is integrated into a circuit board of the interchangeable module.

In some embodiments, the screening platform further comprises materials that sterilize the screening platform. In some embodiments, the screening platform is made from materials selected to be sterilized by one or more of gas sterilization, liquid sterilization, or in an autoclave. In some embodiments, the screening platform is made from plant-based materials so that the screening platform is biodegradable and easily sterilizable, wherein the plant-based materials include one or more of: copper and copper alloys, graphene, or plant-based plastics. In some embodiments, the first CPU is modular and removable from the interchangeable module.

BRIEF DESCRIPTION OF THE DRAWINGS

The disclosure is illustrated by way of example, and not by way of limitation in the figures of the accompanying drawings in which like reference numerals are used to refer to similar elements.

FIG. 13 is a flowchart illustrating data communication between components in the screening platform with harness compute, according to some embodiments.

FIG. 14 is a flowchart illustrating the mechanical interaction of components in the screening platform with harness compute, according to some embodiments.

FIG. 15 is a flowchart illustrating another example of data communication between components in the screening platform with harness compute, according to some embodiments.

DETAILED DESCRIPTION

Figure 1:
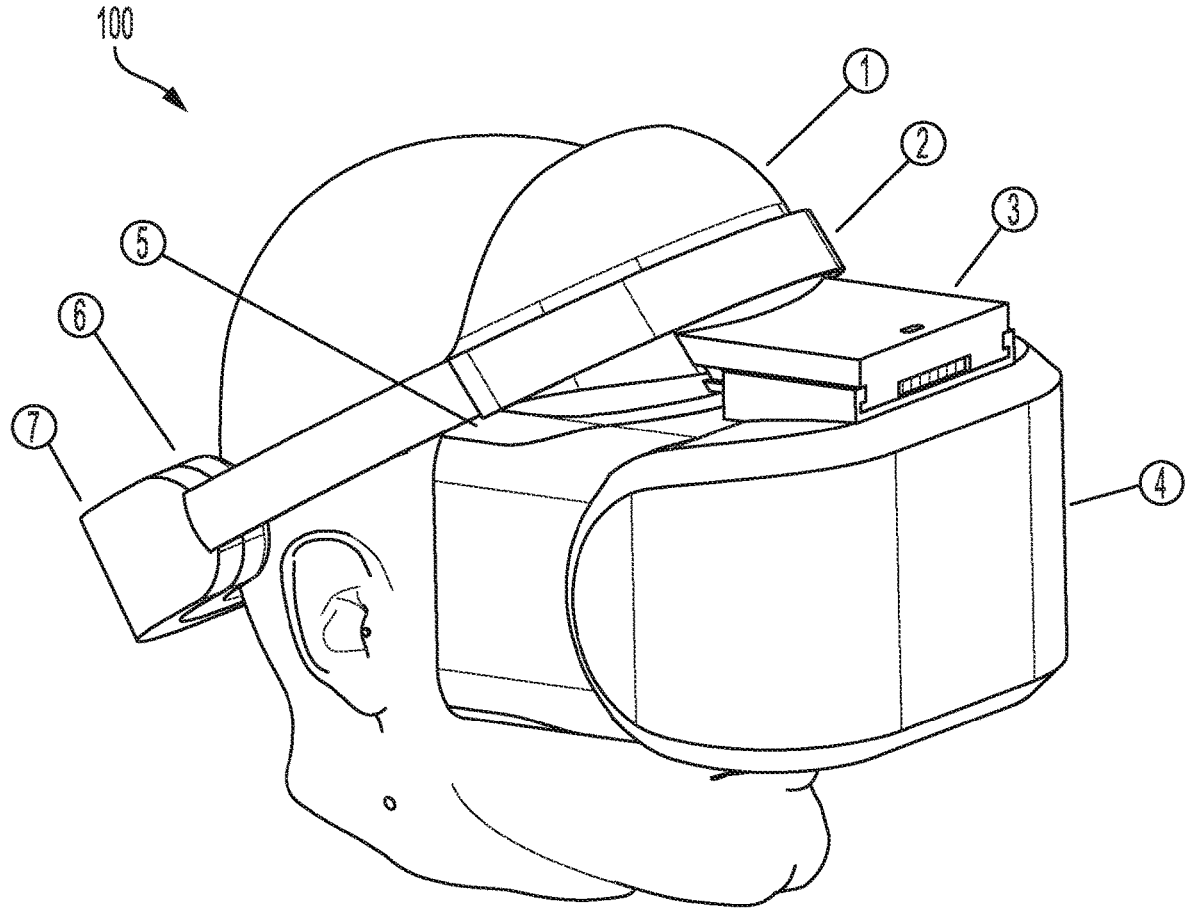
FIG. 1 is a diagram that illustrates the components of an example screening platform with a first type of interchangeable module, according to some embodiments described herein.

Turning to FIG. 1, a diagram of the components of an example screening platform 100 is illustrated according to some embodiments. The screening platform 100 may include forehead padding 1, a harness 2, a harness slide connector 3, an interchangeable module 4, face padding 5, back-head padding 6, and a battery housing 7.

The forehead padding 1, the face padding 5, and the back-head padding 6 may be used to maintain a level of comfort for the patient instead of having the harness directly in contact with the patient's skin. In some embodiments, the parts of the screening platform 100 that are in contact with the patient's skin, such as the forehead padding 1, the harness 2, the face padding 5, and the back-head padding 6, are made with biocompatible polyurethane.

The harness 2 is configured to fit a head of a patient. The harness is designed to fit a center of gravity (COG) box without measuring each patient. In some embodiments, the harness 2 is adjustable to fit a variety of different head shapes and sizes. The measurements and calculations for determining how to place the harness 2 are described in greater detail below with reference to FIG. 7. The preferred embodiment of the harness may weigh 150-350 grams.

The harness 2 ensures that the screening platform 100 remains firmly and comfortably in place on the patient's head. Other attachment mechanisms, such as a cap, helmet or elastic band, that secure the screening platform 100 to the patient's head may be used within the scope of the disclosed subject matter.

The harness 2 may go around the patient's head, and optionally may be designed to tighten to hold the interchangeable module 4 against the patient's head, for example using a tightening knob. Other methods for attaching the harness 2 to the patient's head, such as a second strap that goes over the patient's head, are possible. Other methods for attaching objects such as glasses, hats, goggles, head mounted lights, head mounted magnifying glasses to the patient's head, and many other methods of attachment can be adapted for use in an implementation, and the use of such alternative mounting methods to attach the harness to the patient's head may be employed within the scope of the disclosed subject matter. In some embodiments, the harness or other components of the screening platform 100 include materials that sterilize the screening platform 100, such as copper parts that act as a bactericide; materials selected to be easily sterilized by one or more of gas sterilization, liquid sterilization, or in an autoclave; and/or plant-based materials that make the screening platform 100 biodegradable. In some embodiments, the plant-based materials include one or more of: copper and copper alloys, graphene, or plant-based plastics such as (Polylactide). These materials can easily be augmented to increase sterility, bactericidal, and increased ease of sterility by incorporating ceramic, glass, antimicrobial peptides, silver, ammonium, metal nanoparticles, silver, ammonium, metal nanoparitcles, N,N dodecyl,methyl-poly-ethylenimine wax, polymers, fluroparticles, nanoparticles, copper alloys, and other materials familiar with an expert in the arts.

The harness 2 includes one or more electrical components that are operable to power the interchangeable module 4, perform data processing, store data, etc. For example, the one or more electrical components of the harness 2 may include one or more of rechargeable batteries, a graphical processing unit (GPU), a central processing unit (CPU), random access memory (RAM), storage memory, data and power input and output ports, or an auxiliary port.

In some embodiments, the harness 2 may include wired or non-wired connections that automatically transmit the results of ophthalmic tests to an electronic health record associated with the patient. For example, the CPU described below may include hardware for transmitting the results of ophthalmic tests to other devices. In some embodiments, wireless or wired communication between the harness 2 and an external device enables the operator to manage tests administered to the patient wearing the harness 2 from the external device via data output from the harness 2.

A traditional VR headset may weigh approximately 600 grams, with almost all the mass at the front. The screening platform 100 exerts a torque on the patient's head, which can be uncomfortable after wearing the headset for a prolonged period. The interchangeable module 4 used herein may further increase the mass of the screening platform 100. The interchangeable module 4 needs to be placed in front of the patient's eyes, but other components of the screening platform 100 with significant mass, such as the CPU and/or the battery pack that is within the battery housing 7 may be optimally placed to reduce torque or substantial discomfort that reduces testing accuracy. In some embodiments, avoiding the overwhelming torque reduces dizziness from vestibular compensation of the patient. In some embodiments, where the weight of the batteries is insufficient to reduce torque, a counterweight with a weight of 70-100 grams may be used to reduce torque.

Batteries have significant mass and will typically be part of the CPU. Alternatively, the batteries could be separate from the CPU. If the batteries are mounted separate from the CPU then wires or other electrical conductors (not shown) will be needed to conduct electricity from the batteries to the CPU and the interchangeable module 4. The selection of suitable conductors and their positioning and mounting is well within the skill of those people experienced in the mechanical and electronic arts needed for the design of a screening platform 100.

Figure 2:
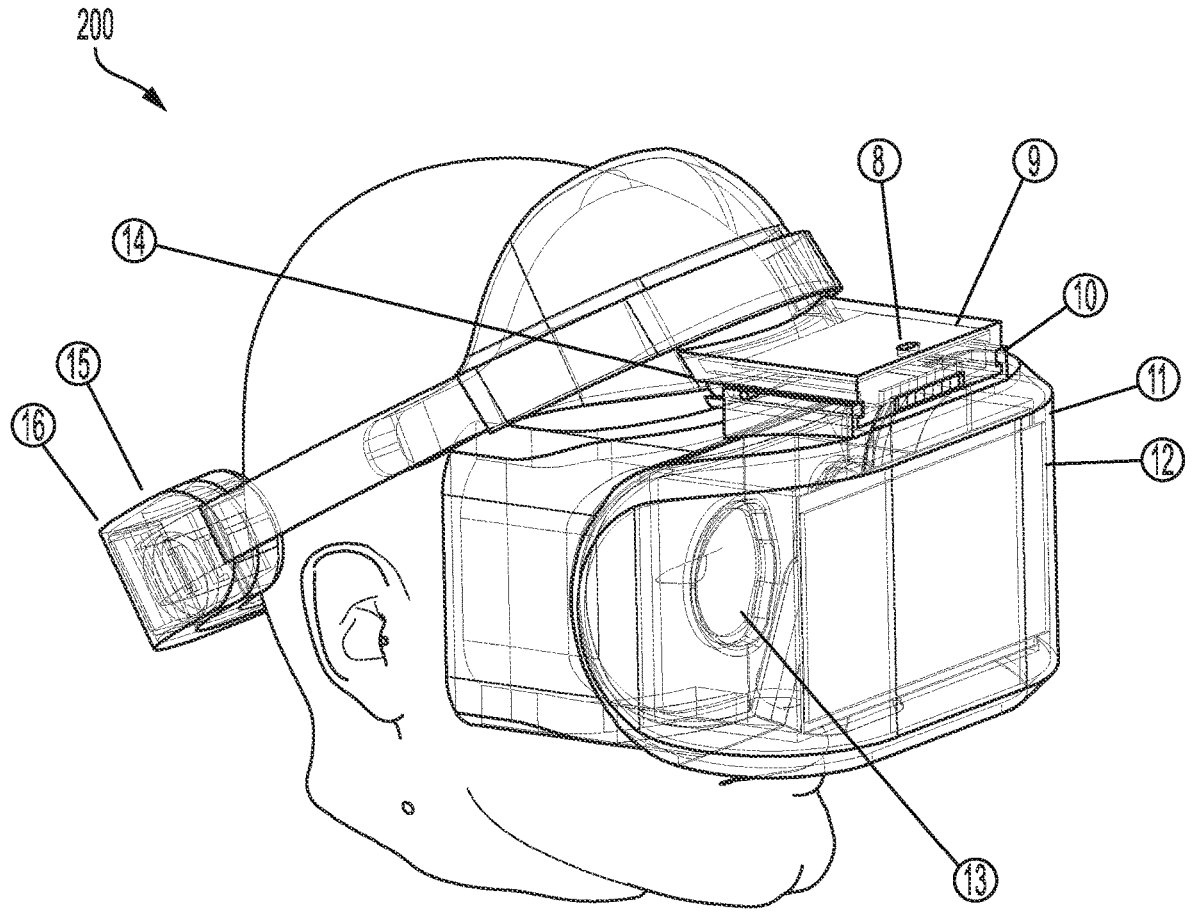
FIG. 2 is a diagram that illustrates some of the internal components of the example screening platform, according to some embodiments described herein.

In the embodiment illustrated in FIG. 2, the harness 2 includes battery housing 7 that holds a battery pack that is mounted on the rear of the harness 2 so that their mass at least in part counters the torque produced by the mass of the interchangeable module 4 on the patient's head. The battery pack includes rechargeable batteries that increase the portability of the screening platform 100 as well as options for communication with remote devices. These batteries can be recharged conventionally through AC power and direct connection via a power cable, redundantly charged while AC power is applied through the harness, or wirelessly charged through induction. The batteries may include a rechargeable lithium ion battery, nickel cadmium batteries, alkali batteries, or any other battery source, whether available at the time of this disclosure or not.

The screening platform 100 includes a first CPU (along with a GPU and RAM) for storage and analysis, a second CPU that is used to control the interchangeable module, and a third CPU that is part of the battery pack. In some embodiments, all three CPUs are on the harness at the same time. For example, the first CPU and the second CPU may be part of the harness slide connector that attaches the interchangeable module 4 to the harness 2 and the third CPU may be in the battery pack. In another example, the first CPU may be part of the harness slide connector, the second CPU may be removably attached to the interchangeable module 4, and the third CPU may be integrated into the battery pack.

The CPU may contain one or more microprocessors, an eye-tracking processor, a graphics processor, memory, other conventional components of a microprocessor-based control system, and may optionally contain additional memory and means for data logging. The CPU may optionally contain means for communication, with outside systems, such communications preferably being conventional digital communications, though customized data formats and communication protocols can be used within the scope of the disclosed subject matter. Examples of such conventional communications include wireless communications such as Bluetooth® (Developed by: Bluetooth Special Interest Group), wifi (IEEE 802.11), Zigbee (IEEE 802.15.4-) or wifi and non-wired communications such as universal serial bus (USB Implementers Forum (USB-IF)) and RS485/Modbus (Modicon/Schneider Electric). The design of microprocessor-based devices is well known to those experienced in the art of electronic design and many designs are possible within the scope of the disclosed subject matter.

The CPU includes hardware for wired or wireless communication to external systems so that the interchangeable module 4 can be controlled by an external computer or tablet-based system (not shown), or in another embodiment, the CPU may act independently, performing its function and storing data for later download to an external computer for further analysis. Optionally, user interface controls, such as buttons, light-emitting diode (LED) lights, and other conventional interface controls may be incorporated into the design of the interchangeable module 4 within the scope of the disclosed subject matter.

The CPU may communicate with an external computer via a universal serial bus (USB) for a wired connection or Bluetooth for a wireless connection. The Bluetooth connection may be preferred because many laptops and other computers/tablets come with Bluetooth installed, and the use of wireless methods such as Bluetooth avoids the difficulties and inconvenience of trailing wires needed with hardware connections. Implementation of this input/output (I/O) interface enables the technology to communicate with a myriad of platforms. However, other means of communication between the CPU and an external computer are also possible within the scope of the disclosed subject matter.

The CPU may also process operator and patient input. For example, the CPU may receive input from the operator via the operator device for changing configurations on the screening platform, with a request to transmit data relating to the ocular evaluations, etc. The operator input may include, for example, a request to transmit the data relating to the ocular evaluations to an electronic medical system in order to update the patient's electronic medical record with the results of the ocular evaluations.

In some embodiments, the CPU or the GPU control, display, and process data from the interchangeable module 4 by employing machine learning algorithms. For example, a processor may include a machine-learning algorithm that receives training data of how various patients performed ocular evaluations based on the order of the different tests and the types of interchangeable modules involved from publicly available and previously procured data sets. The machine-learning algorithm may use the training data to optimize the parameters of the machine learning algorithm to output predictions about the best way to present ocular evaluations to the patient. For example, the machine-learning algorithm may predict that an ideal sequence of ocular evaluations for the patient includes starting with tests that include basic eye tracking, then tests to confirm that the patient is not color blind, then tests involving microperimetry, and ending with tests for traumatic brain injury.

In another example, the machine-learning algorithm may determine that certain tests are redundant or that if the patient is identified as having one type of problem, it is difficult to test for other problems. For example, if the patient is identified as having substance abuse issues, the machine-learning algorithm may determine that the patient should not be tested for certain psychiatric conditions. If a patient is found to have significant cataracts from the interpupillary and eye-tracking cameras in the eye tracking and fails multiple vision tests in the VR module, the machine-learning algorithm can suggest for the provider to not use the retinal imaging module since no meaningful image of the retina could be captured through the opacified lens. Similarly, if a patient comes in with subtle vertical nystagmus that perhaps an emergency front-line provider could not see, the eye-tracking module would be able to transfer that data through the machine learning algorithm and give a quick diagnosis of a drug overdose (phencyclidine in this case) and provide a real-time recommendation for administering benzodiazepines or even intubating the patient rather than calling an ophthalmology consult—saving both the patient's life, hospital resources, and protects the front-line providers.

Real-time machine learning algorithms can be implemented with the combination of VR, retinal imaging, and other modular modalities stored on a processor temporarily.

The processor can access the most up-to-date training algorithm from a cloud-based server and perform edge computing using the harness compute just as the patient finishes the examinations. This edge computing includes but is not limited to the description above for optimization of tests, analysis of imaging modalities (retinal imaging, OCT, etc.) to discover pathologies (early-stage glaucoma, diabetic retinopathy, neuritis, etc.), analyzing the combined functional vision data (VR tests—acuity, perimetry, color blindness, etc.) with pathologic, anatomical imaging data to present to the provider a holistic description (screening +/−preliminary diagnosis) of the patient based on previous data and training algorithms and make a refer/non-refer recommendation (+/−preliminary diagnosis).

An on-board GPU will be leveraged to ingest relevant patient test results and derive machine learning-based recommendations. The GPU may also output graphical data for being displayed on a display device that is part of the interchangeable module 4, such as tests for the patient to perform as part of the ocular evaluations.

The screening platform 100 includes a harness slide connector 3 that attaches the interchangeable modules 4 to the harness 2. The slide connector 3 is discussed in greater detail below with reference to FIG. 5.

The interchangeable module 4 is separable from the screening platform 100 so that the operator can easily switch a first type of interchangeable module 4 with a second type of interchangeable module 4. In some embodiments, the most basic interchangeable module 4 utilizes a display with eye tracking for functional and oculomotor testing through virtual reality.

In some embodiments, the interchangeable module 4 is made from acrylonitrile butadiene styrene (ABS), polycarbonate (PC), a mix of ABS-PC, or nylon. The Young's modulus values may be 2-4 GPa, allowing the module enough strength to avoid shearing with movement and mounting, but also enough flexibility to not shatter if it were to be dropped. The interchangeable module 4 may also include sections made from aluminum for high performance of heat displacement, if needed. In some embodiments, the interchangeable module 4 has a volume of less than or equal to a volume of 8000 cm$^3$ and a weight of 300-800 grams to avoid overwhelming torque on the patient for up to one hour of continuous use. The Young's modulus values may be 69 GPa.

In some embodiments, the screening platform 100 includes materials that reduce heat transfer and improve sterility from the CPU to the skin of a patient. For example, the materials could include carbon fiber laced with copper alloys/nanoparticles and coated with a thermally-insulating material such as dense plastic/rubber. In some embodiments, the materials may also be chosen to improve sterility and allow for commonplace hospital sterilization techniques (autoclave, EtO, H2O2, etc.), including but not limited to copper, stainless steel, carbon fiber, vulcanized rubber, reinforced glass, and the materials listed above. These materials can also be interlaced with antimicrobial materials such as graphene, copper and copper alloys, ceramic, glass, antimicrobial peptides, silver, ammonium, metal nanoparticles, N,N dodecyl,methyl-polyethylenimine. The surface can also be modified using the Wenzel Model to reduce the likelihood of microbial colonization at contact points with the patient. These surfaces can additionally be manufactured, grafted with, or combined with superhydrophobic materials based on the Cassie-Baxter models using materials such as wax, polymers, fluroparticles, nanoparticles, copper alloys, and other materials familiar with an expert in the arts. Similarly, the material can be coated with a material that is self-cleaning or has augmented cleaning under electromagnetic radiation using metals, nanoparticles, or other substances, creating superoxide layers toxic to viruses using metals such as magnesium, gold, gallium and other metals familiar to an expert in the field. The lenses and other parts of the headset, harness, and modules can additionally be coated to further protect the patient and reduce the risk of nosocomial infections.

The interchangeable module 4 has communication capabilities to external computational devices, multiple display output devices, and several types of input devices from both an operator and a patient.

The interchangeable module 4 may include different types of interchangeable modules 4 for performing ocular evaluations. For example, the optical examinations may include visual function examinations, color blindness, refractive errors, intraocular pressure, retinal imaging, tonometry, perimetry, eye-tracking, amblyopia assessment, keratometry, videographic slit lamp microscopy, microperimetry, optical coherence tomography, neurodegenerative disease screening, psychiatric conditions, fluoroscopy, oculomotor exercise coaching, pupillary diameter measurements, saccade measurements, or astigmatism screening. The CPU may integrate or transmit the results for integration with an electronic medical record. The interchangeable module 4 may also perform ocular screening for at least one of the following: ophthalmic diseases, cognitive disorders, psychiatric disorders, neurodegenerative diseases, traumatic brain injury, pharmacologic side effects, or substance abuse. The neurodegenerative diseases include, for example, Alzheimer's, dementia, Parkinson's, and brain tumors. The psychiatric conditions include, for example, depression and post-traumatic stress disorder (PTSD).

Once the ocular evaluation is performed and the interchangeable module(s) 4 generates ocular evaluation data, the GPU on the harness 2 analyzes data from several interchangeable modules 4 concurrently to produce test readouts and patient referral recommendations. For example, the interchangeable module 4 may determine that a patient needs to see an optometrist to update a glasses prescription or that the patient needs to see a neurologist or neurosurgeon because of a possible issue with traumatic brain injury. The computational harness 2 may generate the aforementioned outputs through a cross-analysis of functional and anatomical data from a same angle with respect to the patient's eye due to direct modularity and same-day or immediate temporality.

Turning to FIG. 2, a diagram including some of the internal components of the example screening platform 200 is illustrated according to some embodiments. In this example, the harness slide connector 3 of FIG. 1 includes a harness battery 8, a main printed circuit board (PCB) 9, a connector PCB 10, and connector magnets 14. The harness battery 8 may be used to power the interchangeable module that connects to the slide connector. The harness battery 8 may include a rechargeable lithium ion battery, nickel cadmium batteries, alkali batteries, etc. At the rear of the harness, inside the battery housing illustrated in FIG. 1 a battery PCB 15 and a battery 8 is visible. The battery 8 inside the battery housing is discussed above.

In some embodiments, the main PCB 9 includes the CPU discussed above. The connector PCB 10 may be used to allow different electrical components to interface with the interchangeable module. In some embodiments, the main PCB 9 is placed in a protruding connection point for immediate data transfer to an interchangeable module and isoluation from memory components in the case of an electrical surge.

The mechanical mechanisms coupling of the connector PCB 10 and the interchangeable module include means such as mechanical fittings that have a specific geometry on the interchangeable module such as rails or notches or bayonet fittings that are mirrored in the design of the coupling on the connector PCB 10, thereby snugly holding the connector PCB 10 in place connected to the interchangeable module. Other mechanical mechanisms include magnetic coupling, electromagnetic locking mechanisms (e.g. solenoids), snap fitting, and spring-loaded clips/latches that require a button or lever push to release. Such mechanical means for coupling are well known in the prior art and will be recognized in common products such as those means used to mount a lens on a camera body, a magazine into a handgun or of a battery pack to a hand-held power tool, laptop computer or other electrical or electronic device. Such coupling mechanisms are well known by those experienced in the art of mechanical engineering and any coupling mechanisms which satisfies the need of an implementation of the present disclosure, as described herein may be employed within the scope of the disclosed subject matter.

In addition to clamping the connector PCB 10 to the interchangeable module, the coupling on the connector PCB 10 and its corresponding coupling (not shown) on the interchangeable module must provide electrical connections across the interface between the interchangeable module and the connector PCB 10. The electrical connection needs to contain power and data connections. As discussed herein the typical internal power of a VR headset is low voltage (most current VR headsets use lithium ion battery packs) and so there are few constraints about the connector used to provide power with regard to electrical safety. Examples of similar connectors in use can be seen in the prior art, for example, most laptop computers use electrical connectors to connect the laptop to its lithium ion battery packs. These connectors typically transmit both power from the lithium ion battery and data between the computer and battery management circuit (IEC 62133-2:2017) within the battery pack. A very large selection of electrical connectors is available from electrical component suppliers such as Digikey Electronics (Thief River Falls, MN), and the selection of an appropriate connector is well within the skill of those engineers experienced in the art of electronic design.

In this example, the interchangeable module is a VR module. The VR module includes a screen 11 for each eye, an interchangeable module PCB 12, and lenses 13. The VR module may for example incorporate a display, comprising one or more screens supported by associated electronics. The lenses 13 may be mounted in front of the display to deliver different images to each of the patient's eyes. These two images are used to create the binocular three-dimensional effect of virtual reality or the same technology may be used as specified herein for various types of eye examination. The display, electronics, and lenses 13 may be mounted into a rear case of the VR module.

The display and lenses 13 shown in the VR module can be used to perform certain eye examinations, such as perimetry and testing for color blindness. However, in order to be able to provide a full range of ophthalmic tests at a reasonable cost, it is advantageous to have a number of different optical modules that perform different functions. Different optical modules may have different support electronics, which can all communicate to the same harness CPU. For example, the display will need different electronic control systems than a camera used to obtain image of the retina (discussed below).

The ability to substitute different interchangeable modules allows for increased functionality within the screening platform 200 by allowing data capture and processing via any number of affixed interchangeable modules, as well as modification of the wearer's field of view. Examples of interchangeable modules that may be attached are pupil tracking cameras, retinal imaging cameras, eye covers that can mechanically cover one or both eyes, or a series of refractive lenses. For example, the interchangeable module tracks pupillary eye tracking coordinates for eyes of the patient using at least one of the following illumination sources: visible light, infrared, near ultraviolet light, or narrow-band light. The pupillary eye tracking coordinates are used to guide coordinate-based tests and examinations for other interchangeable modules, such as manual retinal camera alignment of a subsequent interchangeable module through one or more of lead screws, knobs, sliders, or fine-tooth gears through use of coordinates acquired in a separate virtual reality (VR) module. Automated alignment using these coordinates is also possible, with the addition of motor systems such as servos. These examples are included in this application to show the various types of interchangeable modules that can be deployed within the scope of the disclosed subject matter. The examples below are not intended to limit the scope of the disclosed subject matter, but merely to provide examples of what can be achieved within the scope of an implementation of the present disclosure.

For example, a VR module provides a simple display that covers the entire visual field of the wearer (at least 110 degrees). The display can be used for relevant ophthalmic tests such as perimetry, to assess the field of vision of the patient wearing the headset. In perimetry, a small image, such as a point, is displayed in the center of the patient's field of vision, which the patient is instructed to focus on. Small dots of light are momentarily projected around the patient's field of view and when observed the light is registered manually by the patient, typically with an electronic button or similar device that is connected back to either the screening platform 200 or to a computer (not shown) that is controlling the screening platform 200. By correlating the button presses with the positions and timing of the light flashes, the patient's peripheral vision can be determined. Eye tracking is utilized to measure gaze-deviation of the patient (i.e. how many times they looked away from the object in the center of the field-of-view).

Another application that a VR module with a display can perform is a color blindness test. Color blindness is a fairly common condition with approximately 1 in 12 men and 1 in 200 women being affected. There are several different types of color blindness including four types of red-green color blindness: 1) Deuteranomaly is the most common type of red-green color blindness (it makes green look redder), 2) Protanomaly makes red look more green and less bright, and 3) Protanopia and 4) deuteranopia both make the subject unable to tell the difference between red and green. There are two types of red/blue color blindness: 1) Tritanomaly which makes it hard to tell the difference between blue and green, and between yellow and red, and 2) Tritanopia which makes the subject unable to tell the difference between blue and green, purple and red, and yellow and pink. It also makes colors look less bright. The last type of color blindness is the rarer complete color blindness (monochromacy), where the subject can't see any colors at all. To determine the type of color blindness and the level of color vision deficiency, the patient looks at circles of multicolored dots with numbers, symbols, or shapes in them, known as the Ishihara Test. This test is readily performed by projecting the Ishihara images on the display in the screening platform 200 and asking the patient to say the numbers, symbols, or shape if they can see it. Different ophthalmic tests using the same hardware can be run using different software to control the display or other hardware and provide appropriate analysis of the data collected for the ophthalmic test being conducted. Various ophthalmic tests can be run using appropriate hardware and software combinations to allow for appropriate data to be collected allowing for increased sophistication in the data gathered and increased diagnostic capabilities of the provider (e.g a "standard light [31 Apostilbs]" vs a "low light [<10 Apostilbs]" vision test to better gauge multi-dimensional vision functionality and testing more rods than cones through software manipulation (e.g., changing the stimulus intensity on the software side) or hardware manipulation (e.g., adding a light-filter screen/shutter)).

Another type of interchangeable module includes a retinal camera module. For example, the interchangeable module illustrated below in FIG. 4 may be an example of a retinal module. Retinal imaging provides a lot of medically important information not only for diseases of the eye (including glaucoma screening, as uveitis, diabetic retinopathy, vasculitis, retinal vein occlusions, retinal masses, retinal tears and detachments), but also diseases of the circulatory system and nervous system since retinal imaging allows physicians to view blood vessels and nerves directly, operating in their native environment.

In some embodiments, the interchangeable module may be used for non-contact tonometry tests. Non-contact tonometry, also known as pneumotonometry, is a rapid and non-invasive method to measure the intraocular pressure, a parameter that is of great importance in the diagnosis of glaucoma. The recent development of novel miniature non-contact tonometers in the prior art has resulted in it being possible to place a non-contact tonometer in an interchangeable module, in conjunction with eye tracking means for alignment. A small puff of air is directed on the cornea of the eye, and the resulting degree of corneal flattening is measured, from which the intraocular pressure may be calculated.

In some embodiments, the interchangeable module may be used for keratometry tests. The keratometry test measures the shape and curve of the outside cornea, by focusing a circle of light on the cornea and measuring its reflection. This method allows determination of the exact curvature of that area of the cornea's surface and is a diagnostic test for astigmatism. This is a vital test for ophthalmologists and optometrists to prescribe accurate contact prescriptions.

The interchangeable modules discussed herein will enable vision tests to be deployed on the same screening platform to provide a complete assessment for vision screening based on the current gold-standard exams: contrast sensitivity, Amsler grid, Snellen Chart, Color Blindness, and Perimetry, ocular coherence tomography (OCT) for glaucoma, slit lamp microscopy for primary angle closures, and distortion grids and OCT for age-related macular degeneration. Vision tests aim to assess the central (foveal) and peripheral (perimetry) visual acuity of the patient.

One of the major limitations of prior art ophthalmic examination equipment is their purchase cost and their requirement for space. Typically, the equipment is large and bulky, and the cost of equipment alone can exceed over $150,000 for the initial purchase plus an additional $30,000 in maintenance fees every year. Furthermore, some of these instruments—such as the Humphrey's Visual Field Analyzer (Zeiss International, Headquartered in Oberkochen, Germany)—require a well-trained technician and a dark room to conduct the test accurately, further increasing running costs. It has been shown that even though the Humphrey's Visual Field Analyzer is the current clinical standard, there are many variables such as time of day, season, and importantly, technician experience that can have a significant influence on the percent of false-positive answers for patients taking the standard automated perimetry.

Performing these vision tests on the screening platform 200 has the potential to reduce the initial cost over 100-fold while increasing patient throughput in these ophthalmology clinics. The low cost, small form factor, and intentional dark ocular setting of the screening platform 200 allows vision tests to easily be performed and so use of a screening platform 200 has the potential to reduce or eliminate the need for a technician, further reducing human error in running visual tests and also further reducing cost.

Figure 3:
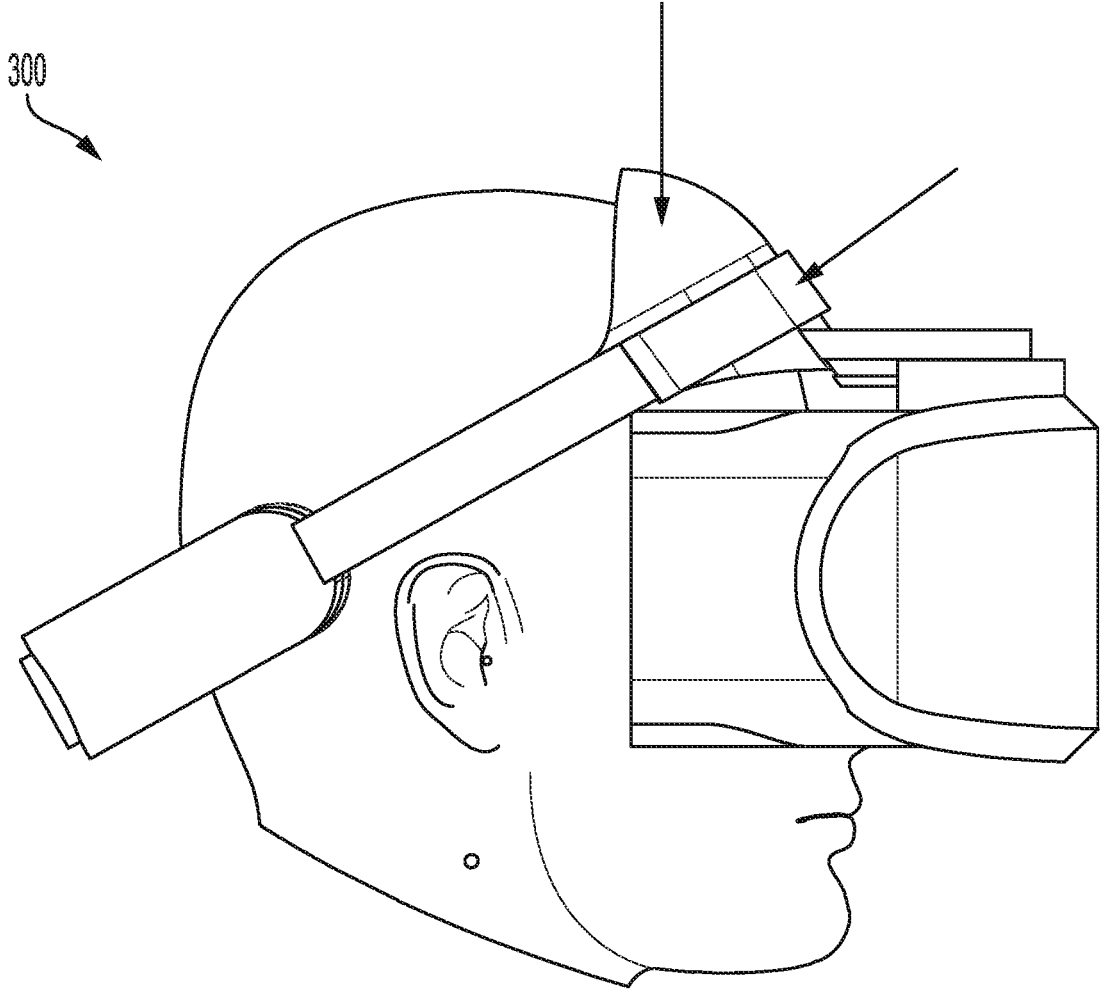
FIG. 3 is a diagram illustrating different forces applied to the harness of the screening platform, according to some embodiments described herein.

Turning to FIG. 3, a diagram of a screening platform 300 illustrating different forces applied to the harness of the screening platform is illustrated according to some embodiments. A patient's forehead experiences forces in two directions: (1) from the top, laying into the head, and (2) from the front, pushing against the back side of the harness. The two different forces help to keep the harness in a stable position.

Figure 4:
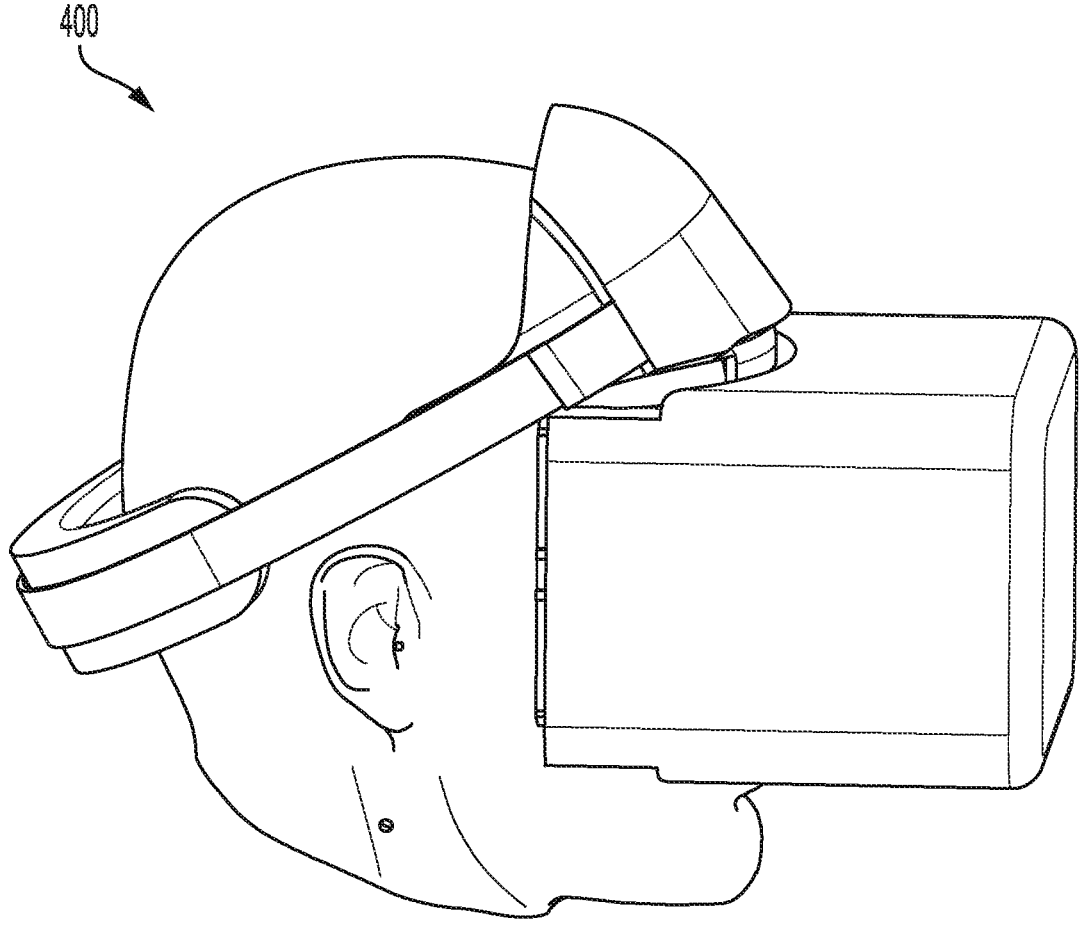
FIG. 4 is a diagram illustrating the components of an example screening platform with a second type of interchangeable module, according to some embodiments described herein.

Turning to FIG. 4, a diagram of a screening platform 400 with a second type of interchangeable module is illustrated according to some embodiments described herein. In this example, the padding on the rear of the harness is a different design than some of the embodiments discussed above. In addition, the read of the harness may be rounder with a greater gap between the harness and the padding and the patient's head.

FIG. 4B is a diagram illustrating an exploded view 450 of the harness of FIG. 4A, according to some embodiments described herein.

Figure 5:
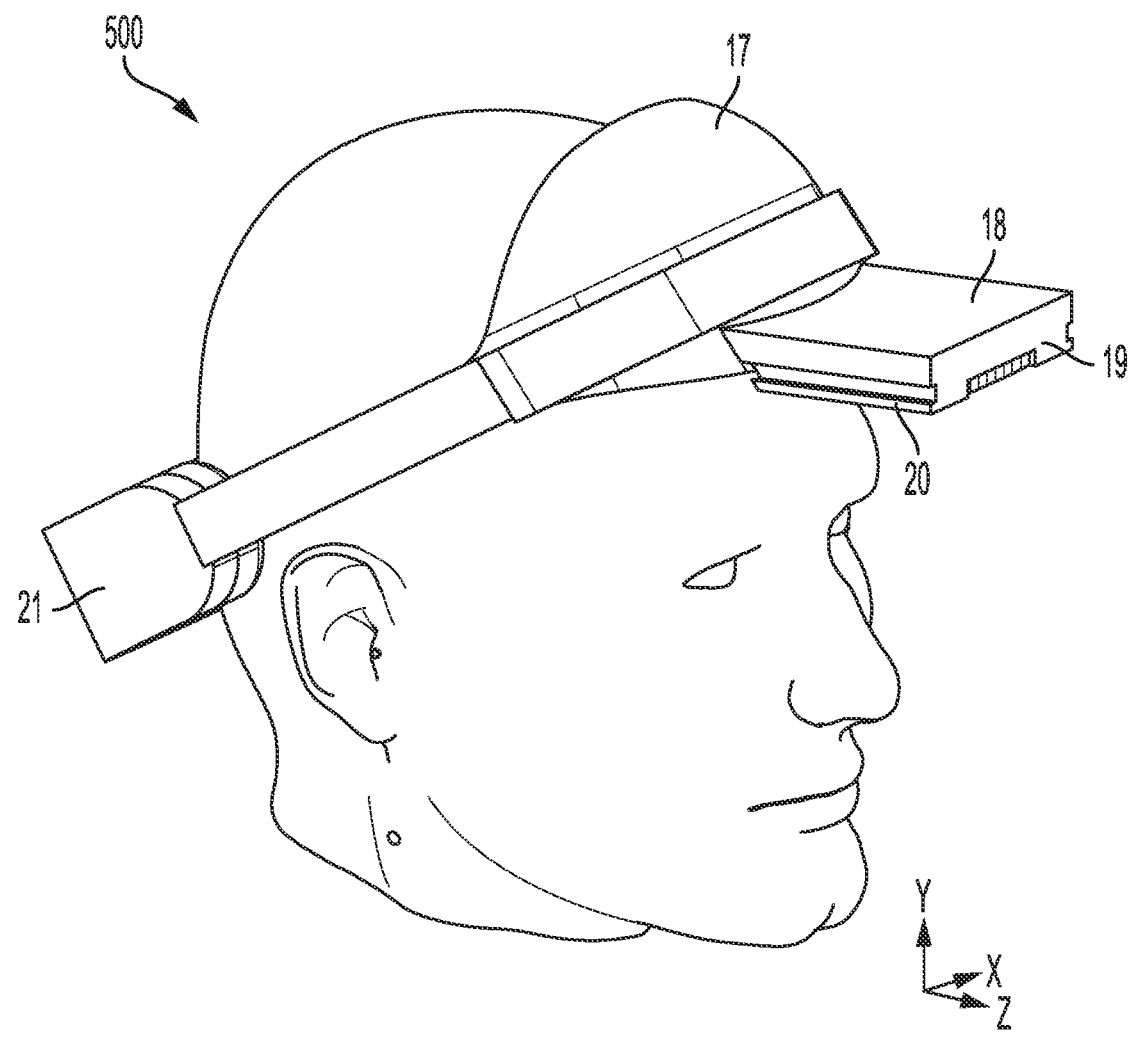
FIG. 5 is a diagram illustrating a first type of harness configuration, according to some embodiments described herein.

Turning to FIG. 5, a diagram of a screening platform 500 with a first type of harness configuration is illustrated according to some embodiments described herein. The screening platform 500 is illustrated with an x-, y-, and z-axis. The harness includes an attachment platform (i.e., the harness slide connector) that does not contact a face of the patient and a separable interchangeable module (not shown) that contacts the face in a light-diminishing fashion. The screening platform 500 includes a head pad with a plastic cover 17, a harness slide connector with a plastic cover 18, electrical connections 19 on the harness slide connector, a mechanical connector 20, and a battery pack 21 on the harness. The mechanical connector 20 includes a ridge for connecting the interchangeable module in the z direction.

The advantage of this design is that it is easy for a patient to wear the harness and for the patient or an operator to add the interchangeable module to the harness slide connector. In some embodiments, the interchangeable module may be removed using friction-based movement with a reasonable force of 400-600 grams/4-6N. In another embodiment, the harness slide connector may include a releasing mechanism. For example, the harness slide connector may include a knob to activate a release mechanism. In this example, the friction is zero and minimal force is needed to install and remove the interchangeable module from the harness.

In some embodiments, the connector and the interchangeable module attach with a male to female connection and a magnetic mating for stable use and a user-friendly interchangeable module removal. This embodiment enables for greater diversity of module-to-face contact, as there is no periorbital frame attachment mechanisms. For example, modules can fit the entirety of the face as the attachment point hovers over the face as opposed to being flush with the face with a frame. This requires for the incorporation of malleable, biocompatible materials where the module meets the face as to enable for a dark environment. As optical coherence tomography technologies are more complex and may require more volume against the face, this is an example of when having greater module attachment flexibility would be preferred. The embodiment below, however, requires malleable materials on the harness with only raw connection mechanisms on the module.

Figure 6:
FIG. 6 is a diagram illustrating an exploded view of the first type of harness configuration, according to some embodiments described herein.
Figure 6:
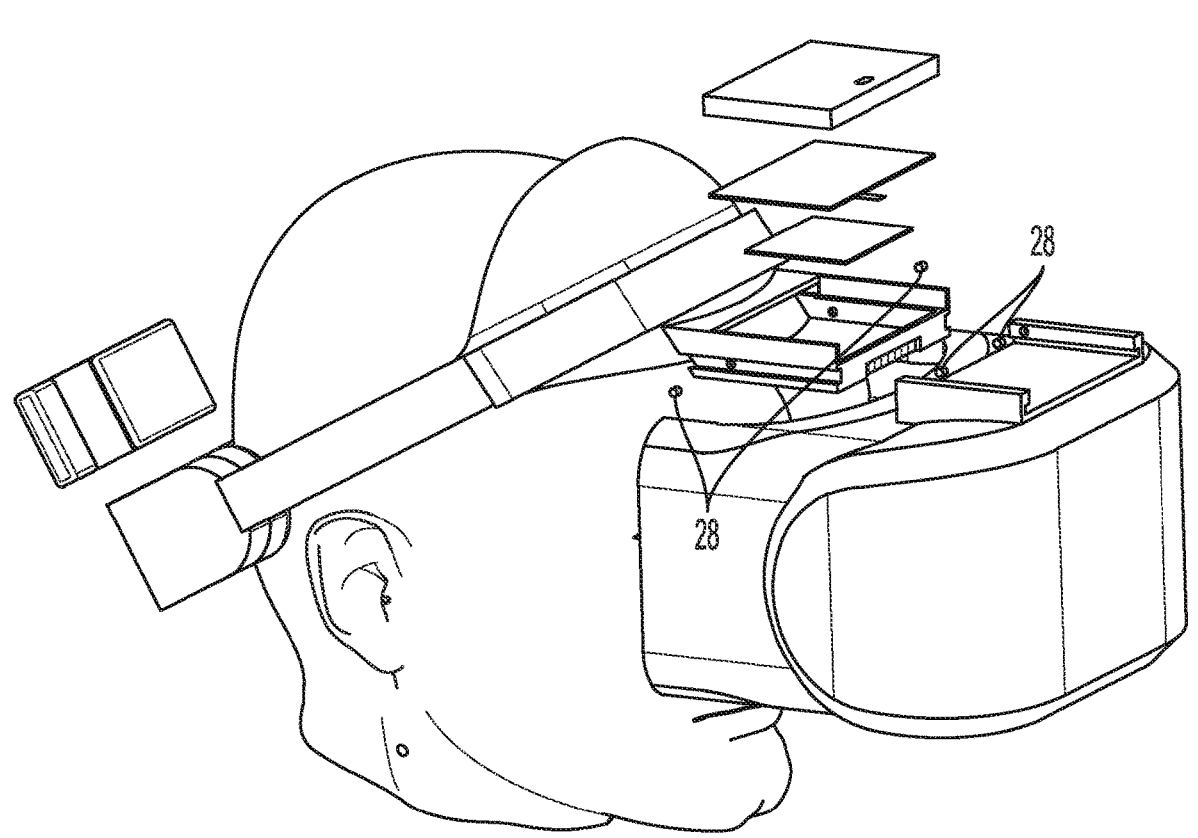

Turning to FIG. 6, a diagram of an exploded view of the screening platform 600 is illustrated including the harness slide connector, according to some embodiments described herein. In some embodiments, the interchangeable module attaches to the harness by sliding along a mechanical connector that forms a rail on the harness slide connector. The harness slide connector and the interchangeable module include magnets 28 that mate to secure the interchangeable module while allowing it to be easily removed without potentially damaging the components with excessive force. The screening platform 600 also includes the battery pack and CPU that fit inside the battery housing.

Figure 7:
FIG. 7 is a diagram illustrating a close-up exploded view of the first type of harness configuration, according to some embodiments described herein.
Figure 7:
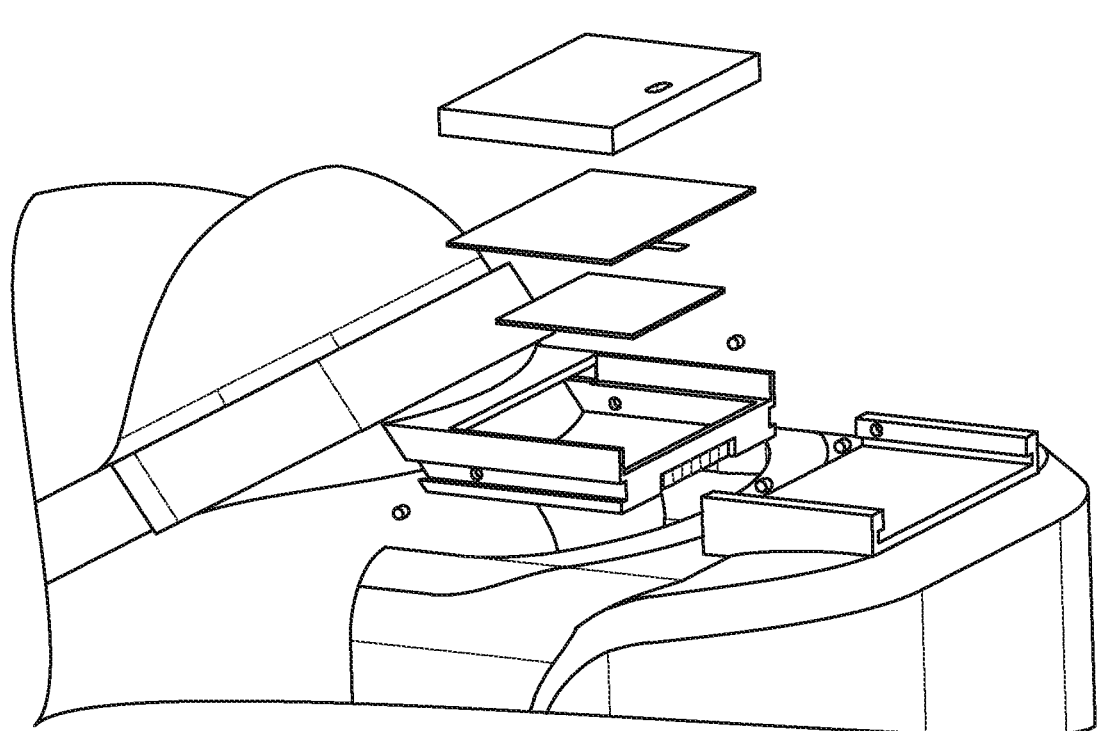

Turning to FIG. 7, a diagram of a close-up exploded view of the first type of harness configuration is illustrated, according to some embodiments described herein. This example shows the top harness slide connector housing, the PCB with the CPU and the GPU for data processing and storage, the PCB for controlling the interchangeable modules, and the bottom top harness slide connector housing.

Figure 8:
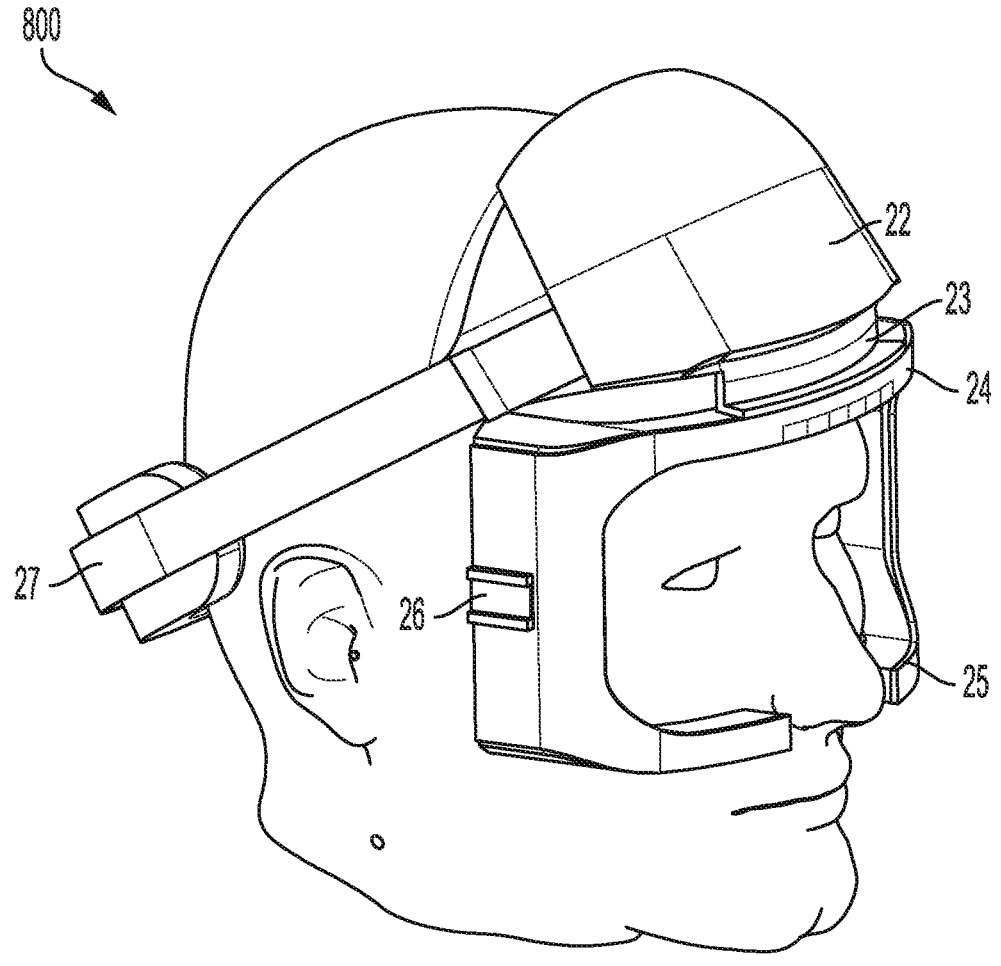
FIG. 8 is a diagram illustrating a second type of harness configuration, according to some embodiments described herein.

Turning to FIG. 8, a diagram of a screening platform 800 with a second type of harness configuration is illustrated according to some embodiments described herein. The screening platform 800 includes a head pad with a plastic cover 22 that holds a PCB with the CPU. A connector 23 connects the harness to a periorbital frame and that moves in the z direction. The periorbital frame includes an electrical connection 24 to connect the electrical components of the harness to the interchangeable module, face padding 25 with a plastic envelope that may include a hood around the nose (not shown), and a mechanical connection 26 for attaching the periorbital frame to the interchangeable module. The screening platform 600 also includes an adjustable strap 27 on the harness.

In this embodiment, the harness includes a periorbital frame to which the interchangeable module is attached. The mechanical connection 26 on the periorbital frame connects a mating mechanical coupling on the interchangeable module such that the interchangeable module is positioned directly in front of the patient's eyes. The periorbital frame is hollow with an opening in front of the patient's eyes such that the patient looks through the opening into the interchangeable module. This embodiment allows for additional module stability against the face and minimal harness movement upon removal, thus allowing for highly replicable testing and acquisition of different forms of data from the same angle with respect to the eye. For example, perimetry and retinal photography can be taken from the same angle due to minimal movement of the harness upon interchanging of the modules, allowing for more accurate correlation of visual deficits with retinal anatomical anomalies.

The attachment mechanisms of the periorbital frame and the interchangeable module are designed such that they matingly connect providing a light proof connection between the periorbital frame and the interchangeable module, thus preventing light from outside the interchangeable module from entering the screening platform 600 from the junction between the periorbital frame and the interchangeable module. This is essential as it creates a completely dark environment that precludes the need for pupillary dilation agents during assays such as retinal photography. Dilating agents take time to be effective and persist for several hours, posing a high level of inconvenience to patients. The attachment mechanisms are further designed such that the interchangeable module is held firmly in place and will not come off the periorbital frame, even if the screening platform 600 is dropped on the floor from several feet; however, the interchangeable module is readily detachable when so desired by the operator.

The mechanical connection 26 for the coupling of the periorbital frame and the interchangeable module include means such as clips, magnets, latches, mechanical fittings which have a specific geometry on the periorbital frame such as rails or notches or bayonet fittings which are mirrored in the design of the interchangeable module, thereby snugly holding the interchangeable module in place. Other mechanical mechanisms include magnetic coupling, electromagnetic locking mechanisms (e.g. solenoids), snap fitting, and spring-loaded clips/latches that require a button or lever push to release. Such mechanical means for coupling are well known in the prior art and will be recognized in common products such as those means used to mount a lens on a camera body, a magazine into a handgun or of a battery pack to a hand-held power tool, laptop computer or other electrical or electronic device. Such coupling mechanisms are well known by those experienced in the art of mechanical engineering, and any coupling mechanisms which satisfies the requirements of an implementation of the present disclosure, as described herein, may be employed within the scope of the disclosed subject matter.

The periorbital frame may include a malleable material that causes the periorbital frame to be flush against the patient's face to provide a dark environment for non-mydriatic examinations. In some embodiments, the interchangeable module is lined with a malleable material to create a flush, light-proof seal against the face. The malleable material of the periorbital frame may be the same as the malleable material that is on the interchangeable module or it is different.

In addition to clamping the interchangeable module to the periorbital frame, the coupling means include an electrical connection 24 from the periorbital frame that attaches to the interchangeable module. The electrical connection 24 contains power and data connections. The electrical connection 24 allows for a secure but reversible attachment, delivery of electrical power, and a two-way electronic data exchange. The typical internal power of a screening platform 600 is low voltage and so there are few constraints about the connector used to provide power with regard to electrical safety. Examples of similar connectors in use can be seen in the prior at, for example, most laptop computers use electrical connectors to connect the laptop to its lithium ion battery packs. These connectors typically transmit both power from the lithium ion battery pack and data between the computer and battery management circuit (IEC 62133-2:2017) within the battery pack. A very large selection of electrical connectors is available from electrical component suppliers such as Digikey Electronics (Thief River Falls, MN), and the selection of an appropriate connector is well within the skill of those engineers experienced in the art of electronic design. Currently, the preferred embodiment for the connective modality is USB-C as it provides a lowprofile, high data and video transfer speed, as well as power transfer; however, one skilled in the arts could easily adapt/upgrade the connectivity port to the most efficient port for video, data, and power transfer.

Figure 9:
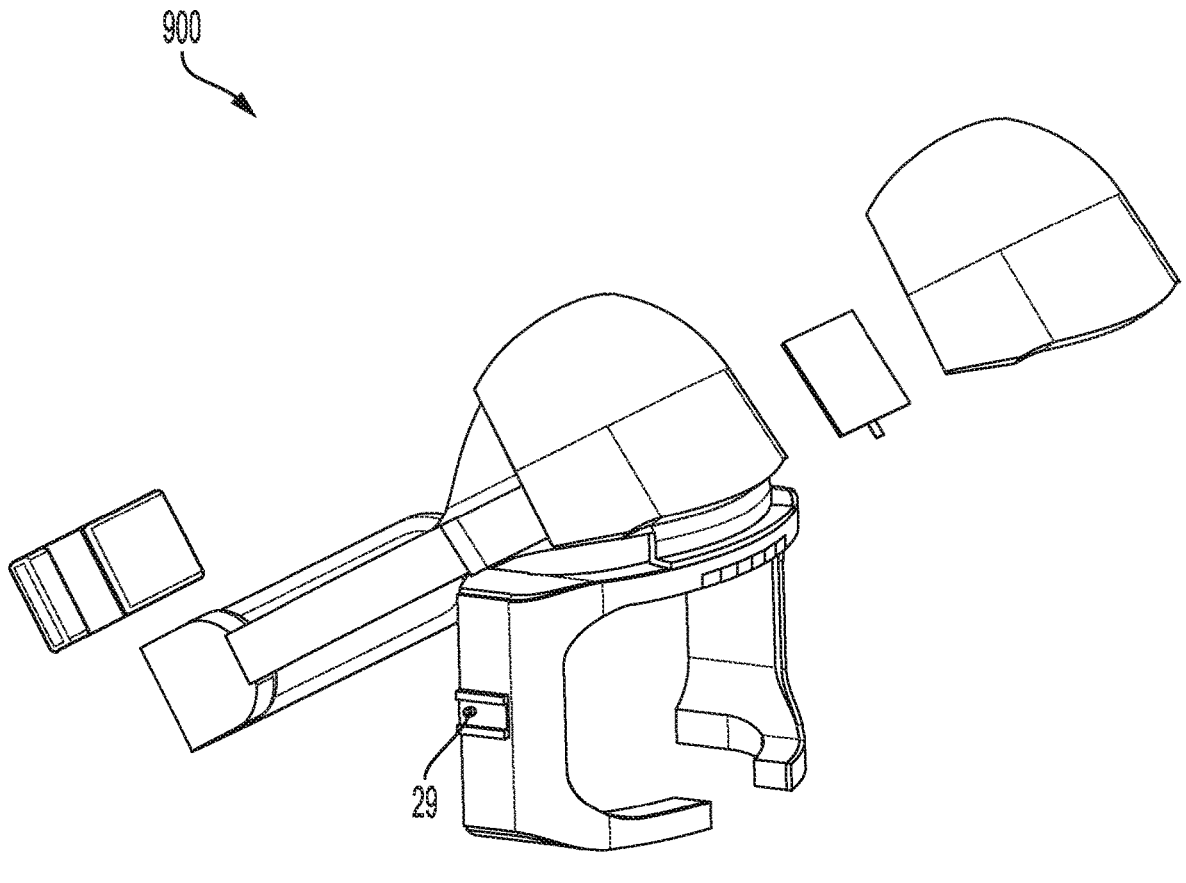
FIG. 9 is a diagram illustrating an exploded view of the second type of harness configuration, according to some embodiments described herein.

Turning to FIG. 9, a diagram 900 of an exploded view of the second type of harness configuration is illustrated, according to some embodiments described herein. In this example, the mechanical connection 26 of FIG. 8 includes a sliding rail and a magnet 29, where the magnet 29 mates with a corresponding magnet on the interchangeable module (not shown). The screening platform 900 also includes the battery pack and CPU that fit inside the battery housing.

Figure 10:
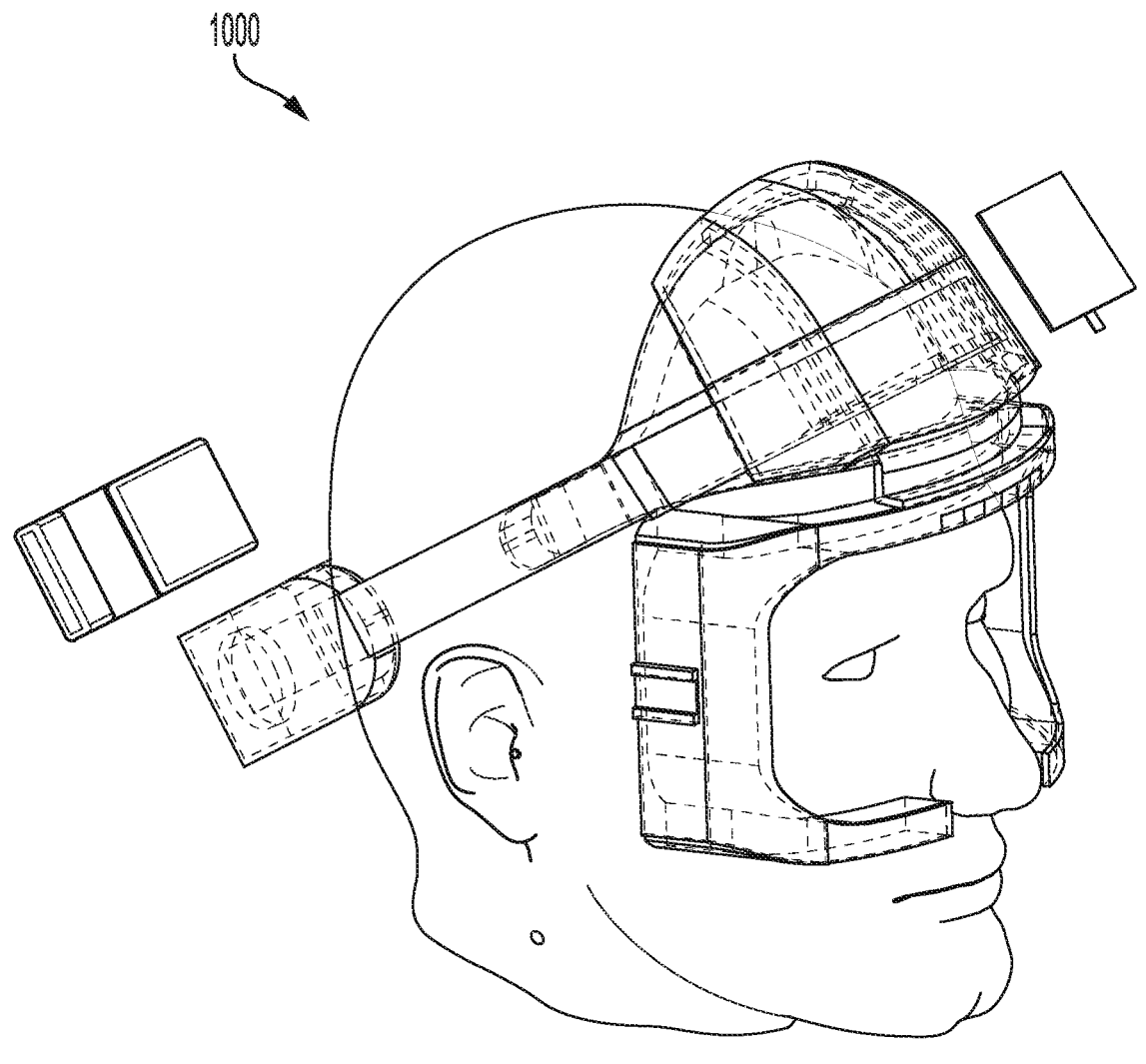
FIG. 10 is a diagram illustrating internal components of the second type of harness configuration, according to some embodiments described herein.

Turning to FIG. 10, a diagram of the screening platform 1000 that includes internal components of the second type of harness configuration is illustrated, according to some embodiments described herein. In this example, the CPU and GPU are positioned underneath the plastic cover on the harness. The screening platform 1000 also includes the battery pack and CPU that fit inside the battery housing.

Figure 11:
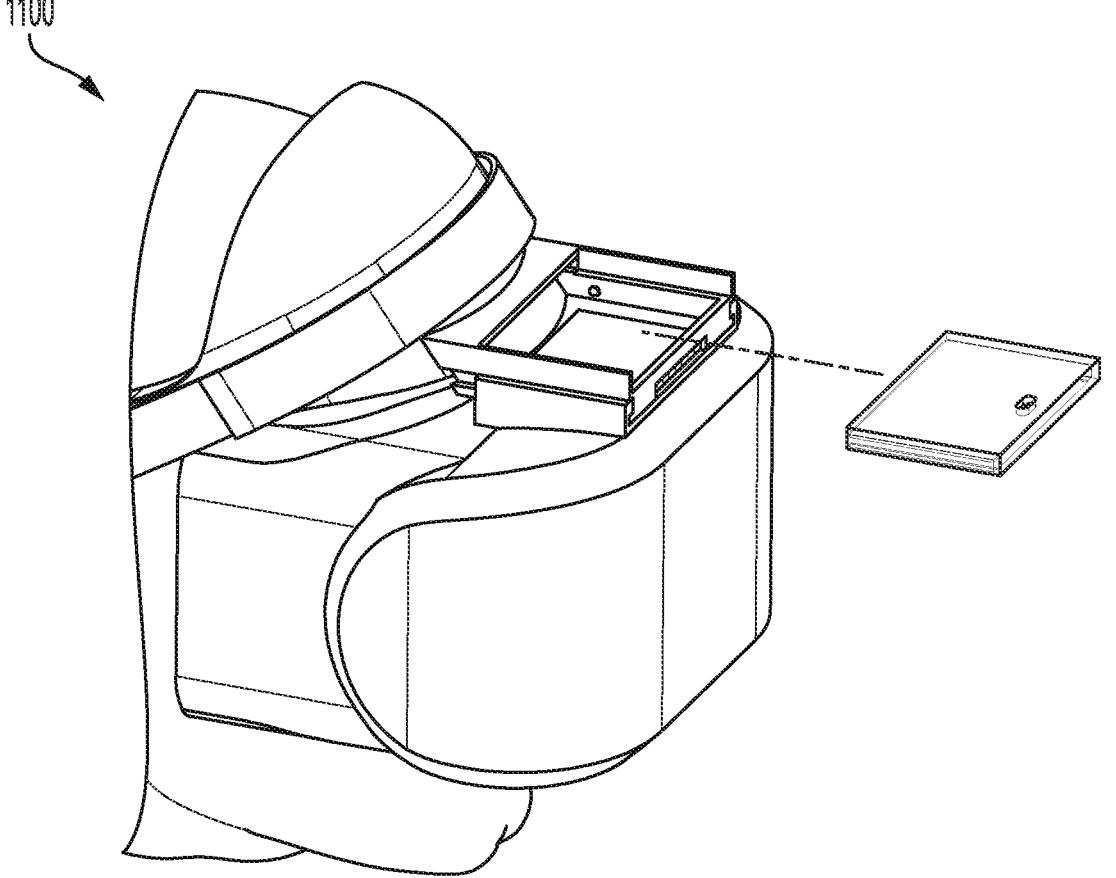
FIG. 11 is a diagram showing alternative locations for the CPU in the screening platform, according to some embodiments.

Turning to FIG. 11, a diagram of another embodiment of the screening platform 1100 where the CPU is modular is illustrated, according to some embodiments described herein. In some embodiments, several different harnesses may be used and so it is advantageous to have a modular CPU that is easily removable from the harness slide connector. As a result, the screening platform 700 maintains centralized computing capabilities. In some embodiments, the housing for the CPU and GPU can be removed from the head harness and transferred to another head harness by means of electrical connection in case an operator chooses not to perform tests in a modular fashion, but rather a single module/exam per headset with several harnesses employed.

Figure 12:
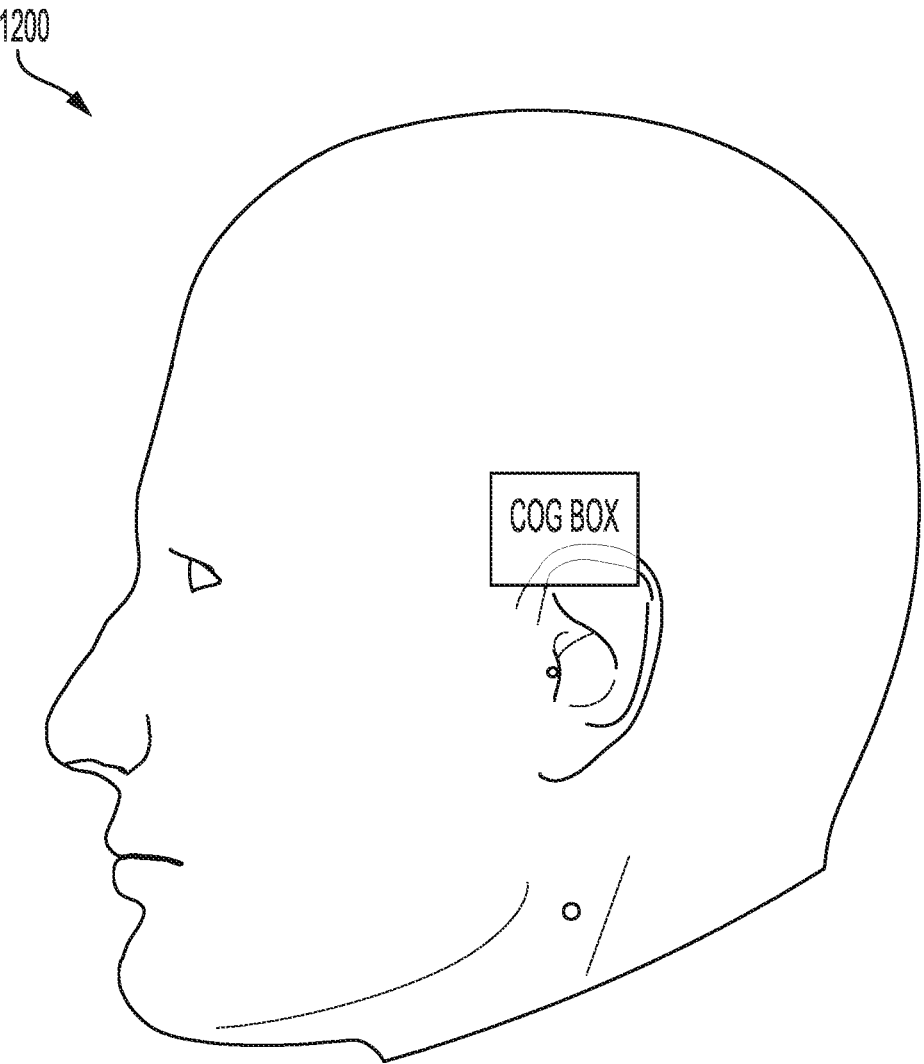
FIG. 12 is a diagram illustrating how to define a center of gravity for the screening platform, according to some embodiments described herein.

Turning to FIG. 12, a diagram of a head 1200 with a determined center of gravity for the screening platform is illustrated according to some embodiments described herein. A tragion is the superior point on the juncture of the cartilaginous flap (tragus) of the ear with the head. An infraorbitale is the lowest point on the anterior border of the bony eye socket. A sellion is the point of the deepest depression of the nasal bones at the top of the nose. The y-axis of the center of gravity box is a vector from the right tragion to the left tragion. The x-axis of the center of gravity box is normal from the y-axis to the right infraorbitale. The origin of the center of gravity box is located at the intersection of the y-axis and a normal passing through the sellion. Once the center of gravity box is determined for a patient, the harness is positioned to overlap with the center of gravity box for ideal placement. Centering weight on this anatomical region reduces torque experienced by the patient, allowing for a more comfortable and accurate assessment experience.

Turning to FIG. 13, a flowchart 1300 illustrating data communication between components in the screening platform with a harness compute is illustrated, according to some embodiments. The system may include external devices, a harness, and interchangeable modules. The external devices may include a user device and a remote.

The external user device may include a smartphone, tablet, desktop computer, etc.; a user interface for interchangeable module examination management and patient data outputs; and an access point to the cloud for patient data upload and download of machine-learning updates to the harness. The remote may include space navigation and object selection for virtual reality programs; a directional pad, trigger, and power button; and wireless and tethered connection options for connecting to the harness.

The harness may include a CPU board, a GPU board, and a power source. The CPU board is the central data relay and includes data downloaded from the interchangeable module and redirected to the GPU; intra-patient data storage and uploaded to module servos; inter-patient data compilation and storage; data exported to a cloud-compatible device via Bluetooth or a wired connection; and accessory management, such as a hand-held remote. The GPU board performs central data processing and includes ocular image processing and real-time machine-learning analysis of module data. The power source is from a tethered user device or an independent battery mounted to the harness.

The interchangeable modules each include unique examination of vision health, such as functional vision capabilities and anatomical health, such as that of the retina; virtual reality, retinal imaging, optical coherence tomography, tonometry; it may contain automated components managed through cross-module data sharing; and is attached to the harness through mechanical, electrical, and/or magnetic components.

FIG. 14 is a flowchart 1400 illustrating the mechanical interaction of components in the screening platform with harness compute, according to some embodiments. The screening platform system includes an external device and a remote connected to the harness, which is connected to a VR module and a retinal imaging module.

FIG. 15 is a flowchart 1500 illustrating another example of data communication between components in the screening platform with harness compute, according to some embodiments. In this embodiment, the external devices are described as performing some of the steps performed by the harness in FIG. 13. Specifically, the external devices may include a smartphone, tablet, desktop computer, etc.; a user interface for interchangeable module examination management and patient data outputs; an access point to the cloud for patient data upload and download of machine learning updates to the harness; ocular image processing; real-time machine learning analysis of module data; inter-patient data compilation and storage; data exported to a cloud-compatible device via Bluetooth or a wired connection; accessory management, such as a hand-held remote; and intra-patient data storage and upload to module servos. The remote may include space navigation and object selection for virtual reality programs; a directional pad, trigger, and power button; and wireless and tethered connection options for connecting to the harness.

The harness may include data downloaded from the interchangeable module and redirection to the external device; and physically and electrically connects the external device to the interchangeable modules. The power source may be from a tethered smart device or an independent battery mounted to the harness.

The interchangeable modules each include unique examination of vision health, such as functional vision capabilities and anatomical health, such as that of the retina; virtual reality, retinal imaging, optical coherence tomography, tonometry; it may contain automated components managed through cross-module data sharing; and is attached to the harness through mechanical, electrical, and/or magnetic components.

What is claimed is:

1. A screening platform that enables comprehensive ocular evaluations, wherein the screening platform is modular, comprising:

a harness that is configured to fit a head of a patient and that includes one or more electronic components that are operable to power a plurality of interchangeable modules;

the plurality of interchangeable modules with communication capabilities to external computational devices, multiple display output devices, and one or more types of input devices from both an operator and the patient, wherein the plurality of interchangeable modules are separable from the screening platform;

a battery pack that is mounted on a rear of the harness and that is configured to provide a counterweight to a mass of an interchangeable module of the plurality of interchangeable modules on the head of the patient; and a first central processing unit (CPU) with a graphical processing unit (GPU), wherein the CPU or the GPU controls, displays, and processes data from the plurality of interchangeable modules by employing a machine-learning model, wherein:

the machine-learning model is trained with training data of how different patients performed ocular evaluations based on an order of different tests and types of interchangeable modules;

the machine-learning model is further trained to receive an indication of one or more patient conditions associated with the patient and output tests and corresponding interchangeable modules of the plurality of interchangeable modules based on the indication of the one or more patient conditions; and the machine-learning model outputs an optimization of the tests and an examination order for the patient that are used to identify one or more pathologies associated with one or more ocular conditions and a preliminary diagnosis.

2. The screening platform of claim 1, wherein the harness includes a harness slide connector that couples one or more of the plurality of interchangeable modules to the harness and wherein the harness slide connector contains a second CPU.

3. The screening platform of claim 2, wherein the first CPU stores data including pupillary coordinates acquired by one of the plurality of interchangeable modules for use with one or more other interchangeable modules of the plurality of interchangeable modules.

4. The screening platform of claim 1, wherein the one or more patient conditions associated with the patient include at least one of the following: a psychiatric condition, a substance-abuse condition, or an ocular condition that is different from the one or more ocular conditions output by the machine-learning model.

5. The screening platform of claim 1, wherein the machine-learning model is further trained to perform analysis of data from the plurality of one or more interchangeable modules to determine at least one of the following: ocular pathology ranging from physiologic deficit pathologies, contrast sensitivity, oculomotor function, visual acuity, color blindness, refractive errors, intraocular pressure, retinal imaging, tonometry, perimetry, eye-tracking, amblyopia assessment, keratometry, videographic slit lamp microscopy, microperimetry, optical coherence tomography, neurodegenerative disease screening, psychiatric conditions, fluoroscopy, oculomotor exercise coaching, pupillary diameter measurements, saccade measurements, or astigmatism screening, wherein the data is configured to integrate within an electronic medical record associated with the patient.

6. The screening platform of claim 1, wherein the one or more electrical components of the harness are selected from the group of rechargeable batteries, random access memory (RAM), storage memory, data or power input and output ports, and an auxiliary port.

7. The screening platform of claim 1, wherein the interchangeable module of the plurality of interchangeable modules is selected to perform at least one of the following optical examinations: visual function examinations, contrast sensitivity, oculomotor function, visual acuity, color blindness, refractive errors, intraocular pressure measurements, retinal photography, tonometry, perimetry, eye-tracking-mediated oculomotor testing, amblyopia assessment, keratometry, videographic slit lamp microscopy, microperimetry, optical coherence tomography, neurodegenerative and psychiatric disease screening, fluoroscopy, oculomotor exercise coaching, pupillary diameter measurements, saccade measurements, or astigmatism screening, wherein any of the optical examinations integrate within an electronic medical record.

8. The screening platform of claim 1, wherein the interchangeable module of the plurality of interchangeable modules is configured to perform ocular screening for at least one of the following: ophthalmic diseases, cognitive disorders, psychiatric disorders, neurodegenerative diseases, traumatic brain injury, pharmacologic side effects, or substance abuse.

9. The screening platform of claim 1, wherein a volume defined by each of the plurality of interchangeable modules is less than or equal to a volume of 8000 cm$^3$ as to avoid overwhelming torque on the patient for up to a continuous 1 hour of use.

10. The screening platform of claim 9, wherein avoiding the overwhelming torque reduces dizziness from vestibular compensation of the patient.

11. The screening platform of claim 1, wherein the harness includes a harness slide connector that couples one or more of the plurality of interchangeable modules to the harness by sliding along a mechanical connector that forms a rail on the harness slide connector and wherein the harness slide connector includes magnets that mate to secure the interchangeable module of the plurality of interchangeable modules.

12. The screening platform of claim 1, wherein the first CPU includes wireless communication to external systems, output displays, and processes operator and patient input.

13. The screening platform of claim 1, wherein the harness includes communication capabilities to external computational devices to provide a referral and further screening recommendations to a healthcare provider through a cross-analysis of functional and anatomical data from a same angle with respect to an eye of the patient.

14. The screening platform of claim 1, wherein results of ophthalmic tests are transferred automatically to an electronic health record associated with the patient through a wired or non-wired connection out from the harness.

15. The screening platform of claim 1, wherein the interchangeable module of the plurality of interchangeable modules tracks pupillary eye tracking coordinates for eyes of the patient using at least one of the following illumination sources: visible light, infrared, near ultraviolet light, or narrow-band light.

16. The screening platform of claim 15, wherein the pupillary eye tracking coordinates from the interchangeable module are used to guide coordinate-based tests and examinations for a separate interchangeable module, the separate interchangeable module including one or more of a manual or automatic retinal camera alignment of a subsequent interchangeable module through one or more of lead screws, knobs, sliders, fine-tooth gears, or motors.

17. The screening platform of claim 1, wherein wireless or wired communication between the harness and an external device enables the operator to manage tests administered to the patient wearing the harness from the external device via data output from the harness.

18. The screening platform of claim 1, further comprising a periorbital frame to which the interchangeable module of the plurality of interchangeable modules is attached.

19. The screening platform of claim 18, wherein the periorbital frame includes a malleable material that causes the periorbital frame to be flush against a face of the patient to provide a dark environment for non-mydriatic examinations.

20. The screening platform of claim 1, further comprising an attachment platform that does not contact a face of the patient.

21. The screening platform of claim 20, wherein the interchangeable module is lined with a malleable material to create a flush, light-proof seal against the face.

22. The screening platform of claim 1, wherein a third CPU is integrated into a circuit board of the interchangeable module of the plurality of interchangeable modules.

23. The screening platform of claim 1, further comprising materials that reduce heat transfer from the first CPU to skin of the patient.

24. The screening platform of claim 1, further comprising materials that sterilize the screening platform.

25. The screening platform of claim 1, wherein the screening platform is made from materials selected to be sterilized by one or more of gas sterilization, liquid sterilization, or in an autoclave.

26. The screening platform of claim 1, wherein the screening platform is made from plant-based materials so that the screening platform is biodegradable, wherein the plant-based materials include one or more of: copper and copper alloys, graphene, or plant-based plastics.

27. The screening platform of claim 1, wherein the first CPU is modular and removable from the interchangeable modules.

* * * * *